United States Patent
Benser et al.

(10) Patent No.: US 7,519,425 B2
(45) Date of Patent: Apr. 14, 2009

(54) TIERED THERAPY FOR RESPIRATORY OSCILLATIONS CHARACTERISTIC OF CHEYNE-STOKES RESPIRATION

(75) Inventors: Michael Benser, Valencia, CA (US); Eric Falkenberg, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 642 days.

(21) Appl. No.: 10/968,730

(22) Filed: Oct. 18, 2004

(65) Prior Publication Data

US 2005/0165457 A1 Jul. 28, 2005

Related U.S. Application Data

(63) Continuation-in-part of application No. 10/765,624, filed on Jan. 26, 2004, now Pat. No. 7,421,296.

(51) Int. Cl.
*A61N 1/00* (2006.01)
(52) U.S. Cl. ..................................................... 607/42
(58) Field of Classification Search .............. 600/26, 600/27, 484, 529, 531–538, 547; *A61M 21/00; A61B 5/08, A61B 5/02, 5/05; A61N 1/00*
See application file for complete search history.

(56) References Cited

U.S. PATENT DOCUMENTS

| | | | |
|---|---|---|---|
| 4,712,555 A | 12/1987 | Thornander et al. | 128/419 PG |
| 4,788,980 A | 12/1988 | Mann et al. | 128/419 PG |
| 4,830,008 A | 5/1989 | Meer | 128/421 |
| 4,940,052 A | 7/1990 | Mann et al. | 128/419 PG |
| 4,944,298 A | 7/1990 | Sholder | 128/419 PG |
| 5,466,254 A | 11/1995 | Helland | 607/123 |
| 6,266,564 B1 | 7/2001 | Hill et al. | 607/6 |
| 6,314,323 B1 | 11/2001 | Ekwall | 607/23 |
| 6,415,183 B1 | 7/2002 | Scheiner et al. | 607/42 |
| 6,641,542 B2 * | 11/2003 | Cho et al. | 600/529 |
| 6,904,320 B2 * | 6/2005 | Park et al. | 607/17 |
| 7,363,085 B1 * | 4/2008 | Benser et al. | 607/42 |
| 2002/0193697 A1 | 12/2002 | Cho et al. | 600/529 |

(Continued)

FOREIGN PATENT DOCUMENTS

EP 0505195 A2 9/1992

(Continued)

OTHER PUBLICATIONS

Garrido-Garcia H, ("Treatment of chronic ventilatory failure using a diaphragmatic pacemaker.", Spinal Cord. May 1998;36(5):310-4.).*

(Continued)

*Primary Examiner*—George Manuel

(57) ABSTRACT

An exemplary method includes delivering a maintenance therapy that aims to prevent occurrence of apnea, sensing information, based at least in part on the information, determining if apnea exists and, if apnea exists, delivering a termination therapy that aims to terminate the apnea. An exemplary implantable device includes an input for information pertaining to respiration and control logic to call for overdrive pacing at a first rate that aims to minimize occurrence of a respiratory condition, to analyze the information for occurrence of the respiratory condition and, upon occurrence of the respiratory condition, to call for overdrive pacing at a higher rate. Other exemplary methods, devices, systems, etc., are also disclosed.

21 Claims, 19 Drawing Sheets

U.S. PATENT DOCUMENTS

| | | | |
|---|---|---|---|
| 2003/0153953 A1 | 8/2003 | Park et al. | 607/17 |
| 2003/0153954 A1* | 8/2003 | Park et al. | 607/17 |
| 2004/0138719 A1 | 7/2004 | Cho et al. | 607/42 |
| 2005/0119586 A1* | 6/2005 | Coyle et al. | 600/538 |

FOREIGN PATENT DOCUMENTS

| | | | |
|---|---|---|---|
| EP | 0505195 A3 | | 9/1992 |
| EP | 1462146 A1 | | 9/2004 |
| JP | 2003250915 A | * | 9/2003 |
| WO | WO 01/41868 A1 | | 6/2001 |
| WO | WO 02/087433 A1 | | 11/2002 |

OTHER PUBLICATIONS de Chazal, Philip, Member IEEE, et al., "Automated Processing of the Single-Lead Electrocardiogram for the Detection of Obstructive Sleep Apnoea," *IEEE Trans. Biomedical Eng.*; vol. 50, No. 6 (2003), pp. 686-696.

Sériès, F. et al., "*Functional Genomics of Sleep and Circadian Rhythm Selected Contribution: Influence of Genioglossus Tonic Activity on Upper Airway Dynamics Assessed by Phrenic Nerve Stimulation*," J Appl Physiol; vol. 92 (2002), pp. 418-423.

Sin, Don D., MD, MPH et al., "Effects of Continuous Positive Airway Pressure on Cardiovascular Outcomes in Heart Failure Patients with and without Cheyne-Stokes Respiration," *Circulation*: vol. 102 (2000), pp. 61-66.

Frédéric Sériès, et al., "Assessment of Upper Airway stabilizing Forces with the Use of Phrenic Nerve Stimulation in Conscious Humans," *J Appl Physiol*, 2003; vol. 94(2), pp. 2289-2295.

T. Wiβkirchen, et al., "Zentrales Schlafapnoe Syndrom und Periodische Atmung," *Therap Umschau*, 2000; vol. 57(7), pp. 458-462.

Notice of Allowance, mailed Dec. 6, 2007: Related U.S. Appl. No. 10/765,625.

Final Office Action, mailed Mar. 4, 2008: Related U.S. Appl. No. 10/765,624.

Notice of Allowance, mailed Jul. 9, 2008: Related U.S. Appl. No. 10/765,624.

* cited by examiner

EXEMPLARY FLOW PATTERNS
300

EXEMPLARY METHOD
900

- ① $UA > UA_L$ INDICIA OF ADEQUATE UA PATENCY

- ② $F > F_L$ INDICIA OF INADEQUATE FLOW (MAX, AREA, ETC.)

- ③ DELIVER STIMULATION AT END OF EXPIRATION

- ④ $UA > UA_L$ INDICIA OF ADEQUATE UA PATENCY

- ④ DELIVER STIMULATION TO IMMEDIATELY AUGMENT (OPTIONAL)

- ⑤ $F > F_L$ INDICIA OF INADEQUATE FLOW (MAX, AREA, ETC.)

- ⑥ DELIVER STIMULATION AT END OF EXPIRATION

EXEMPLARY SCENARIO
1500

TIDAL VOLUME VERSUS TIME

ENERGY VERSUS TIME

TIDAL VOLUME

TIERED THERAPY FOR RESPIRATORY OSCILLATIONS CHARACTERISTIC OF CHEYNE-STOKES RESPIRATION

RELATED APPLICATION

This application is a continuation-in-part of copending U.S. patent application Ser. No. 10/765,624, filed Jan. 26, 2004, entitled "Termination of Respiratory Oscillations Characteristic of Cheyne-Stokes Respiration", which is incorporated by reference herein. This application is related to copending U.S. patent application Ser. No. 10/765,625, filed Jan. 26, 2004, entitled "Augmenting Hypoventilation", which is incorporated by reference herein.

TECHNICAL FIELD

Exemplary methods, devices, systems, etc., presented herein generally relate to prevention and treatment of various respiratory conditions using stimulation.

BACKGROUND

Central apnea and hypopnea stem from insufficient central nervous system drive and result in inadequate ventilation. Many of those afflicted also suffer from congestive heart failure (CHF). A particular form of apnea and hypopnea is known as Cheyne-Stokes Respiration (CSR), in which tidal volume oscillates between hyperpnea and hypopnea and/or apnea with a periodicity on the order of about 70 seconds. In general, CSR occurs during sleep and therefore CSR can preclude quality sleep through induction of apnea-terminating arousals. CSR also burdens the heart with transient episodes of hypoxia and surges in sympathetic tone, which can exacerbate CHF.

Various studies have examined how respiratory therapy may benefit CHF patients that experience CSR. For example, a study by Sin et al., "Effects of continuous positive airway pressure on cardiovascular outcomes in heart failure patients with and without Cheyne-Stokes respiration", *Circulation*, 102: 61-66 (2000), indicates that continuous positive airway pressure improves cardiac function in patients with CHF who also have CSR and central sleep apnea. In particular, this study indicated that continuous positive airway pressure improved left ventricular ejection fraction and resulted in a risk reduction in the mortality-cardiac transplantation rate. However, the approach taken by Sin et al. relies on an external pressure generating device that provides positive airway pressure. As discussed herein, various techniques to terminate respiratory oscillation characteristic of CSR may be implemented using an implantable device that may optionally provide cardiac therapy as well.

SUMMARY

An exemplary method includes delivering a maintenance therapy that aims to prevent occurrence of apnea, sensing information, based at least in part on the information, determining if apnea exists and, if apnea exists, delivering a termination therapy that aims to terminate the apnea. An exemplary implantable device includes an input for information pertaining to respiration and control logic to call for overdrive pacing at a first rate that aims to minimize occurrence of a respiratory condition, to analyze the information for occurrence of the respiratory condition and, upon occurrence of the respiratory condition, to call for overdrive pacing at a higher rate. Other exemplary methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

Figure 1:
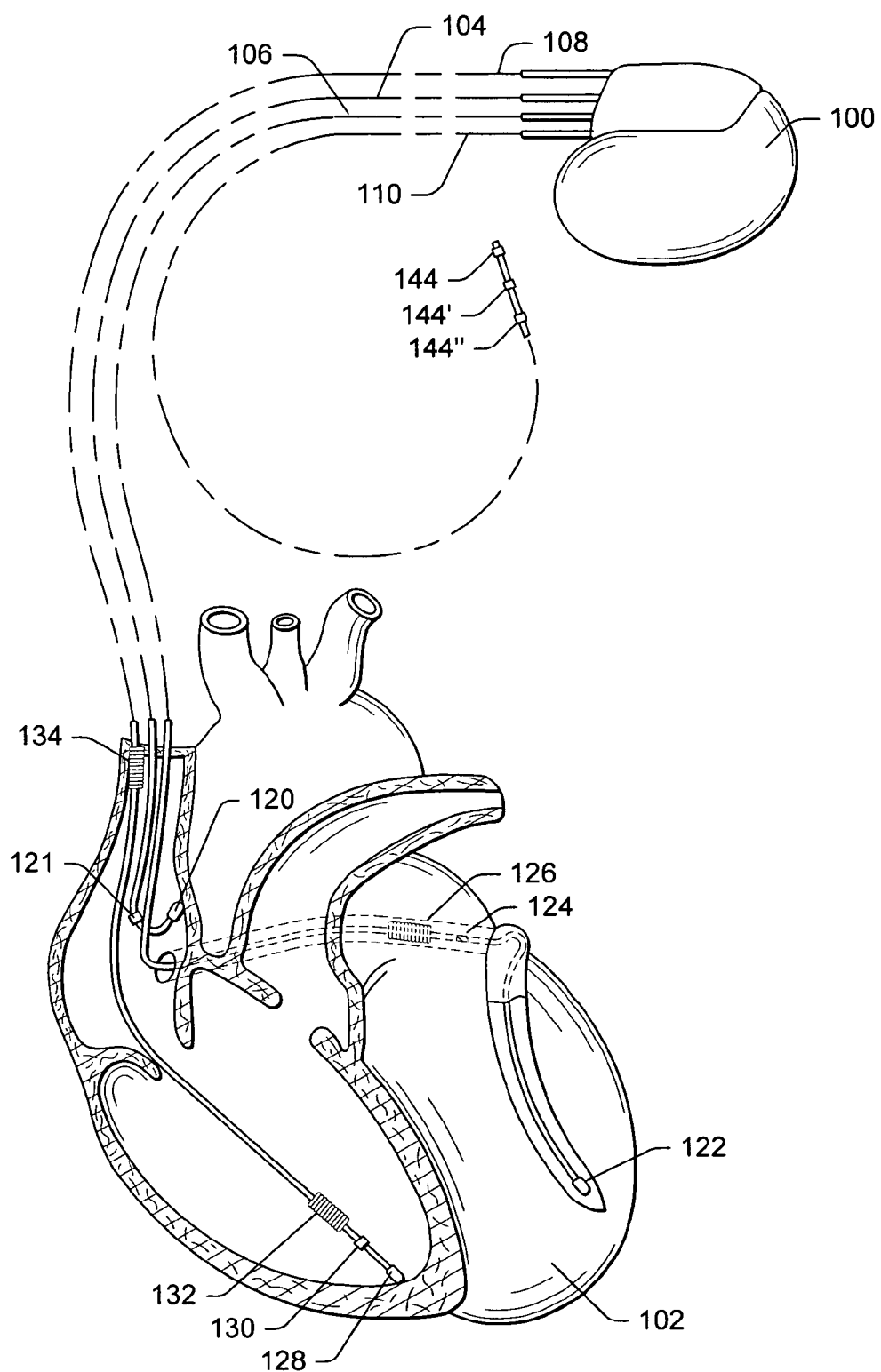
FIG. 1 is a simplified diagram illustrating an exemplary implantable stimulation device in electrical communication with at least three leads implanted into a patient's heart and at least one other lead for delivering stimulation and/or shock therapy. Exemplary devices may have lesser leads as well.

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims.

Overview

Tiered therapies for respiratory conditions, disclosed herein, optionally include maintenance therapy as an initial tier. In general, maintenance therapy aims to prevent occurrence of a respiratory condition. However, should the respiratory condition occur, then a higher tier of therapy may be implemented. An initial tier typically relies on a cardiac pacing therapy while a higher tier may rely on a cardiac pacing therapy and/or artificial diaphragm activation. In general, a higher tier of therapy aims to terminate an existing respiratory condition. Other therapies disclosed herein, that rely on diaphragm activation, may also act to prevent and/or terminate various respiratory conditions.

Artificial diaphragm activation may be achieved via phrenic nerve stimulation, diaphragm stimulation and/or other tissue stimulation. Artificial diaphragm activation can augment and/or act as a replacement to intrinsic means of diaphragm activation. An exemplary mechanism disclosed herein aims to provide diaphragm activation to terminate or break out of Cheyne-Stokes Respiration (CSR). In particular, such a mechanism calls for diaphragm activation to dampen respiratory oscillations characteristic of CSR. Diaphragm activation is optionally achieved using stimulation power proportional to tidal volume, flow, or other indicator of respiration. As discussed herein, the term "proportional" includes linearly proportional, nonlinearly proportional and step-wise proportional. With respect to step-wise proportionality, a variable may vary to some degree prior to a step-wise proportional change in stimulation energy or power. Further, as discussed herein, one or more respiration related limits may act to call for a zero order (e.g., constant) stimulation energy or power or inhibition of stimulation. Yet further, energy or power may be based on a nondecreasing monotonic relationship with respect to increasing tidal volume.

Various studies, however, have associated certain forms of artificial diaphragm activation with upper airway collapse. Thus, in this regard, an exemplary mechanism may optionally aim to: (i) elucidate when an upper airway may collapse, (ii) reduce risk of upper airway collapse and/or (iii) prevent or terminate artificial diaphragm activation upon occurrence of conditions indicative of upper airway collapse or imminent upper airway collapse. Where appropriate, an exemplary mechanism terminates CSR without a significant risk of upper airway collapse.

An exemplary stimulation device is described below followed by a discussion of upper airway dynamics and various exemplary mechanisms that aim to terminate CSR. Various exemplary methods follow that include tiered therapies. The aforementioned exemplary stimulation device (described in more detail below) is optionally used to implement such exemplary tiered therapy methods.

Exemplary Stimulation Device

The techniques described below are intended to be implemented in connection with any stimulation device that is configured or configurable to stimulate nerves, stimulate muscle tissue and/or stimulate and/or shock a patient's heart (e.g., myocardial muscle tissue).

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of nerves (e.g., autonomic nerves, phrenic nerves, etc.) and/or muscle tissue other than myocardial tissue. In addition, the device 100 includes a fourth lead 110 having, in this implementation, three electrodes 144, 144', 144" suitable for stimulation of nerves (e.g., autonomic nerves, phrenic nerves, etc.) and/or muscle and/or detection of other physiologic signals that may be used by the implanted system to modify stimulation parameters. The lead 110 may be positioned in and/or near a patient's heart, near a nerve (e.g., an autonomic nerve, a phrenic nerve, etc.) or near muscle tissue other than myocardial tissue within a patient's body and remote from the heart. The right atrial lead 104, as the name implies, is positioned in and/or passes through a patient's right atrium. The right atrial lead 104 optionally senses atrial cardiac signals and/or provides right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of nerves and/or muscle tissue.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves, other nerves and/or tissue. Such a lead may include cardiac pacing, nerve and/or muscle stimulation functionality and may further include bifurcations or legs. For example, an exemplary coronary sinus lead includes pacing electrodes capable of delivering pacing pulses to a patient's left ventricle and at least one electrode capable of stimulating a nerve (e.g., autonomic nerve, a phrenic nerve, etc.) and/or other tissue.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating a nerve and/or other tissue; such an electrode may be positioned on the lead or a bifurcation or leg of the lead. For example, an exemplary right ventricular lead includes pacing electrodes capable of delivering pacing pulses to a patient's left ventricle and at least one electrode capable of stimulating a nerve (e.g., autonomic nerve, a phrenic nerve, etc.) and/or other tissue.

Figure 2:
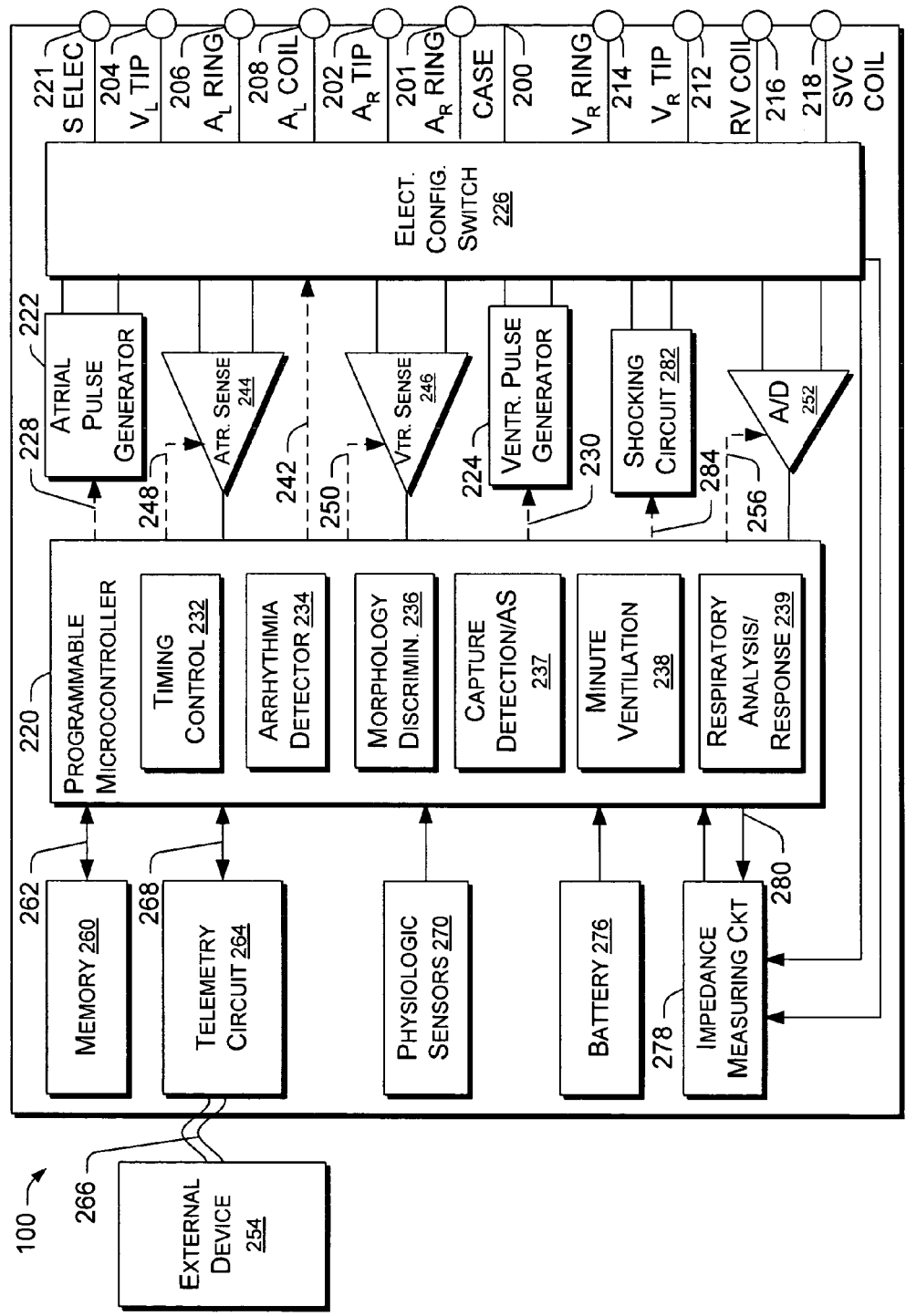
FIG. 2 is a functional block diagram of an exemplary implantable stimulation device illustrating basic elements that are configured to provide cardioversion, defibrillation, pacing stimulation and/or autonomic nerve stimulation or other tissue and/or nerve stimulation. The implantable stimulation device is further configured to measure position and/or movement.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to nerves (e.g., autonomic nerves, phrenic nerves, etc.) and/or muscle tissues. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation and/or treating respiratory issues via cardiac, nerve and/or muscle stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable nerve and/or muscle stimulation electrodes is also possible via these and/or other terminals (e.g., via a stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable nerve and/or muscle stimulation electrodes is also possible via these and/or other terminals (e.g., via the stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to nerves and/or other muscle tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrioventricular (AV) delay, interatrial conduction (A-A) delay, or interventricular conduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes, for example, an arrhythmia detector 234, a morphology discrimination module 236, a capture detection and/or autosensitivity module 237, a minute ventilation (MV) response module 238 and a respiratory analysis and/or response module 239. These components can be utilized by the stimulation device 100 for determining desirable times to administer various therapies. The aforementioned components may be implemented in hardware as part of the microcontroller 220, or as software/firmware instructions programmed into the device and executed on the microcontroller 220 during certain modes of operation. Various exemplary methods described herein are optionally implemented as logic, which may be embodied in software and/or hardware.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture. The sensing circuits 244, 246, via switches, etc., may also be used to sense information related to respiration (e.g., chest movement monitoring, etc.).

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. Other features for arrhythmia detection, confirmation, etc. are discussed below and may be suitable as appropriate. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Nerve, muscle and/or cardiac signals are also optionally applied to inputs of an analog-to-digital (A/D) data acquisition system 252. The data acquisition system 252 is, for example, configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve and/or muscle stimulation lead through the switch 226 to sample signals across any of desired electrode (e.g., unipolar) or electrodes (e.g., multipolar).

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further includes one or more physiologic sensors 270. For example, a physiologic sensor commonly referred to as a "rate-responsive" sensor is optionally included and used to adjust pacing stimulation rate according to the exercise state of the patient. However, one or more of the physiologic sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, diurnal changes in activity (e.g., detecting sleep and wake states), etc. Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the one or more physiologic sensors 270 may also be external to the stimulation device 100, yet still be implanted within or carried by the patient.

In particular, the one or more physiologic sensors 270 optionally include a position and/or movement sensor mounted within the housing 200 of the stimulation device 100 to detect movement in the patient's position or the patient's position. Such a sensor may operate in conjunction with a position and/or movement analysis module (e.g., executable in conjunction with the microcontroller 220). The position and/or movement sensor may be implemented in many ways. In one particular implementation, the position sensor is implemented as an accelerometer-based sensor capable of measuring acceleration, position, etc. For example, such a sensor may be capable of measuring dynamic acceleration and/or static acceleration. In general, movement of the patient will result in a signal from the accelerometer. For example, such an accelerometer-based sensor can provide a signal to the microcontroller 220 that can be processed to indicate that the patient is undergoing heightened physical exertion, moving directionally upwards or downwards, etc.

Further, depending on position of the implanted device and such a movement sensor, the sensor may measure or monitor chest movement indicative of respiratory characteristics. For example, for a typical implant in the upper chest, upon inspiration, the upper chest expands thereby causing the implanted device to move. Accordingly, upon expiration, the contraction of the upper chest causes the device to move again. Such a movement sensor may sense information capable of distinguishing whether a patient is horizontal, vertical, etc.

While respiratory information may be obtained via the one or more physiologic sensors 270, the aforementioned minute ventilation (MV) sensor 238 may sense respiratory information related to minute ventilation, which is defined as the total volume of air that moves in and out of a patient's lungs in a minute. A typical MV sensor uses thoracic impedance, which is a measure of impedance across the chest cavity wherein lungs filled with air have higher impedance than empty lungs. Thus, upon inhalation, impedance increases; whereas upon exhalation, impedance decreases. Of course, a thoracic impedance may be used to determine tidal volume or measures other than minute ventilation.

With respect to impedance measurement electrode configurations, a right ventricular tip electrode and case electrode may provide current while a right ventricular ring electrode and case electrode may allow for potential sensing. Of course, other configurations and/or arrangements may be used to acquire measurements over other paths (e.g., a superior-inferior path and a left-right path, etc.). Multiple measurements may be used wherein each measurement has a corresponding path.

Direct measurement of phrenic nerve activity may be achieved using a cuff or other suitable electrode appropriately positioned in relationship to a phrenic nerve. For example, a cuff electrode substantially surrounding the right phrenic nerve in the thoracic cavity can detect signals indicative of intrinsic respiratory drive (at least to the right hemidiaphragm). Such signals are typically of amplitude measured in microvolts (e.g., less than approximately 30 microvolts). Sensing may be coordinated with other events, whether natural event or events related to some form of stimulation therapy. As discussed herein, some degree of synchronization may occur between calling for and/or delivering stimulation for diaphragm activation and sensing of neural activity and/or other indicators of respiration and, in particular, inspiration.

While respiratory characteristics are optionally measured with a signal such as a thoracic impedance signal, alternatively or in addition to, central respiratory drive is optionally determined via sensing of phrenic nerve activity. In one example, phrenic nerve (e.g., right and/or left phrenic nerve) activity is sensed using one or more electrodes on or proximate to the phrenic nerve. In another example, diaphragmatic myopotentials are sensed (e.g., EMG, etc.) using one or more electrodes on or proximate to the diaphragm. Plethysmography may be used in measuring any of a variety of variables that related to respiration.

Other means for detection include measuring the intrathoracic pressure associated with respiration or from stress and/or strain gauges measuring changes in the dimensions of the thoracic cavity including the lungs. Respiratory information may also be inferred by sensing information that relates to mechanisms altered by respiration. For example, body chemistry varies in response to respiration. Hence, chemical parameters such as tissue or blood pH, $PCO_2$, $O_2$, $PO_2$ may be sensed and either used to infer, confirm and/or augment other respiratory information.

Signals generated by the one or more physiologic sensors 270 and/or the MV sensor 238 or impedance sensor are optionally processed by the microcontroller 220 in determining whether to apply one or more therapies.

More specifically, with respect to a movement sensor, the microcontroller 220 may receive a signal from an accelerometer-based sensor that may be processed to produce an acceleration component along a vertical axis (i.e., z-axis signal). This acceleration component may be used to determine whether there is an increased or decreased level of activity in the patient, etc. The microcontroller 220 optionally integrates such a signal over time to produce a velocity component along the vertical direction. The vertical velocity may be used to determine a patient's position/activity aspects as well, such as whether the patient is going upstairs or downstairs. If the patient is going upstairs, the microcontroller 220 may increase the pacing rate or invoke an orthostatic compensator to apply a prescribed stimulation therapy, especially at the onset. If the patient is traversing downstairs, the device might decrease a pacing rate or perhaps invoke the MV response module to control one or more therapies during the descent. The MV response module may provide information to be used in determining a suitable pacing rate by, for example, measuring the thoracic impedance from the MV sensor 238, computing the current MV, and comparing that with a long-term average of MV. As described herein, MV information and/or other sensed information may be used to determine an appropriate respiratory therapy.

The microcontroller 220 can also monitor one or more of the sensor signals for any indication that the patient has moved from a supine position to a prone or upright position. For example, the integrated velocity signal computed from the vertical acceleration component of the sensor data may be used to determine that the patient has just stood up from a chair or sat up in bed. A sudden change in the vertical signal (e.g., a positive change in a direction normal to the surface of the earth), particularly following a prolonged period with little activity while the patient is sleeping or resting, confirms that a posture-changing event occurred. The microcontroller 220 optionally uses this information as one potential condition for deciding whether to invoke, for example, an orthostatic compensator to apply cardiac pacing therapy for treating orthostatic hypotension. Other uses are described in more detail below.

While a two-axis accelerometer may adequately detect tilt with respect to acceleration of gravity, the exemplary stimulation device 100 may also or alternatively be equipped with a GMR (giant magnetoresistance) sensor and circuitry that detects the earth's magnetic fields. Such a GMR sensor and circuitry may be used to ascertain absolute orientation coordinates based on the earth's magnetic fields. The device is thus able to discern a true vertical direction regardless of the patient's position (i.e., whether the patient is lying down or standing up). Where three-axes are measured by various sensors, coordinates may then be taken relative to the absolute orientation coordinates from the GMR. For instance, as a person sits up, the axial coordinates of an accelerometer-based sensor might change by 90°, but the sensor signals may be calibrated as to the true vertical direction based on the output of a GMR sensor and circuitry.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration rate and/or tidal volume; measuring thoracic or other impedances for determining shock or other thresholds; detecting when the device has been implanted; measuring stroke volume; and detecting the opening of heart valves, etc. The impedance measuring circuit 278 is advantageously coupled to the switch 226 so that any desired electrode may be used.

The impedance measuring circuit 278 may also measure impedance related to lung inflation. Such a circuit may use a case electrode, an electrode positioned in or proximate to the heart and/or another electrode positioned within or proximate to the chest cavity. Various exemplary methods described below rely on impedance measurements to determine lung inflation and/or optionally inspiratory vagal excitation, which can inhibit excitatory signals to various muscles (e.g., diaphragm, external intercostals, etc.).

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As already mentioned, the device 100 of FIGS. 1 and 2 has features suitable to call for and/or deliver appropriate diaphragm activation. With respect to calling for diaphragm activation, the respiratory analysis module 239 may be used and with respect to delivery, any of the various pulse generators, electrodes, etc., may be used. In general, diaphragm activation involves direct or indirect phrenic nerve stimulation, transvenous phrenic nerve stimulation and/or direct or indirect diaphragm muscle stimulation.

Direct phrenic nerve stimulation uses one or more electrodes or poles (e.g., magnetic stimulation) in close proximity (e.g., typically in contact with) to a phrenic nerve. Such electrodes or poles may be positioned in the cervical region or other regions of the phrenic nerves which may be superior to the heart, proximate to the heart and/or inferior to the heart, noting that such positioning and/or stimulating may consider risk of parasitic or inadvertent cardiac activation.

Transvenous phrenic nerve stimulation involves positioning one or more electrodes or poles in a vessel proximate to a phrenic nerve. For example, the right phrenic nerve runs along the intimal tissue of the superior vena cava and the left phrenic nerve runs near the innominate vein. In general, stimulation energy and power for tranvenous stimulation exceeds that of direct phrenic nerve stimulation. The diaphragm is segmented into approximately two hemidiaphragms; thus, stimulation of a right phrenic nerve may act to activate primarily the right hemidiaphragm while stimulation of a left phrenic nerve may act to activate primarily the left hemidiaphragm. Various studies indicate that an adequate level of respiration may be achieved via activation of a single hemidiaphragm. As described herein, diaphragm activation may involve right and/or left hemidiaphragm activation.

Stimulation of the diaphragm from one or more electrodes or poles positioned proximate to or in the diaphragm may achieve adequate respiration for various purposes disclosed herein. In one example, a pair of electrodes are positioned intramuscularly proximate to the region where a phrenic nerve innervates a hemidiaphragm. In this example, stimulation delivered via the pair of electrodes acts to cause diaphragm activation via nerve and/or muscle excitation. Various studies indicate that inferior placement or positioning of electrodes in or on the diaphragm is suitable to achieve diaphragm activation. Of course, other arrangements may be used where appropriate. Further, an implantable device capable of delivering stimulation for diaphragm activation may be placed subcutaneously in or near the abdomen in a manner that is less invasive than that associated with a pectoral pocket implant.

Figure 3:
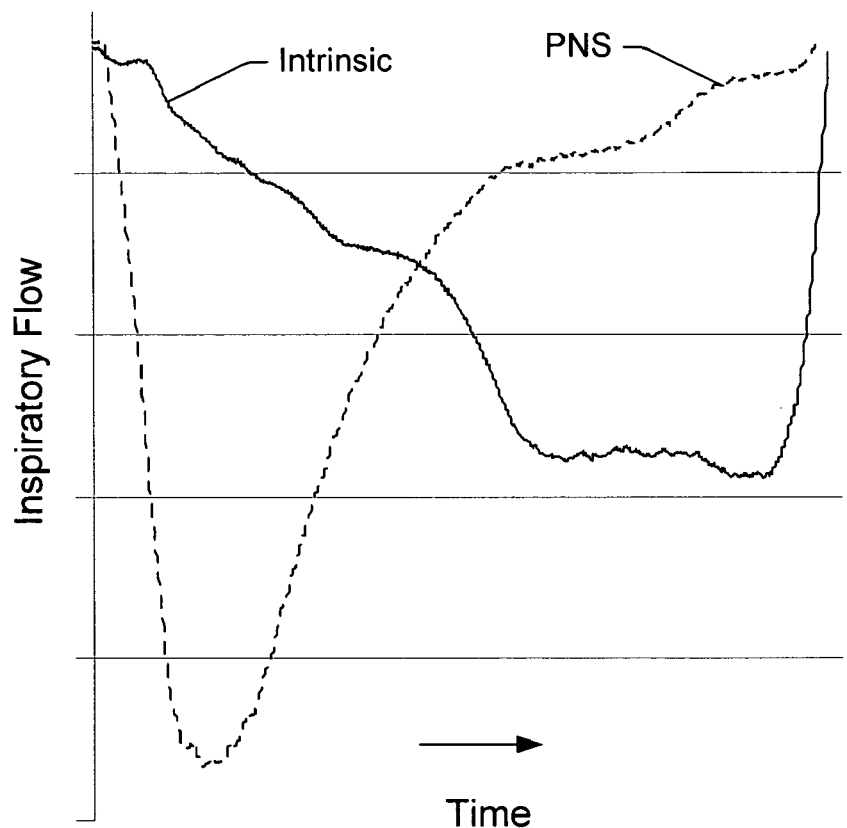
FIG. 3 is a plot of exemplary inspiratory flow patterns associated with intrinsic inspiration and inspiration due at least in part to artificial diaphragm activation.

FIG. 3 shows a plot 300 of inspiratory flow versus time for inspiration associated with intrinsic respiration and for inspiration due to phrenic nerve stimulation, typically referred to as PNS. According to the plot 300, intrinsic respiration is associated with a normal inspiration pattern having a late flow peak whereas PNS results in an inspiration pattern having an early flow peak. While the data presented in the plot 300 are only examples, as actual intrinsic or PNS patterns may differ, they serve to exhibit typical differences between intrinsic respiration and respiration induced via PNS.

In the PNS case, flow increases fairly dramatically after the onset of the stimulation. If the upper airway has insufficient patency during this increase in flow, the upper airway may collapse. Some studies have identified the oro-pharynx region as the most likely site of airway collapse because of a lack of support by rigid cartilaginous or bony structures such as those present in nasal and laryngeal airways. For example, obstructive sleep apnea (OSA) patients frequently experience airway collapse in the pharyngeal region. OSA is typically associated with normal intrinsic phrenic nerve activity and inadequate airway patency, which may be due in part to excessive tissue mass around the airway. In contrast to obstructive sleep apnea, central sleep apnea (CSA) is mainly due to an instability of the breathing control system. More specifically, Cheyne-Stokes respiration (CSR) is a breathing disorder characterized by recurrent episodes of central hypopneas or apneas and hyperventilation, which as described by Cheyne and Stokes, may show a crescendo-decrescendo pattern of respiration. CSR or periodic breathing is often associated with heart failure, while other forms of CSA are often associated with neurological disorders especially those involving the brainstem (see, e.g., Wisskirchen et al., "Central sleep apnea syndrome and Cheyne-Stokes respiration," *Ther Umsch.* 2000 July; 57 (7): 458-62). In general, CSR may be considered a subset of central apnea; however, central apneas are not always associated with the oscillator crescendo and decrescendo patterns of CSR.

While the plot 300 shows data for inspiration, knowledge of characteristics of the expiratory part of the respiratory cycle may also benefit various exemplary mechanisms for diaphragm activation. For example, in normal respiration, during early expiration, laryngeal width is typically low while pharyngeal cross-sectional area is typically at a cycle maximum. As expiration continues, an increase typically occurs in laryngeal width and, at the end of expiration, a drop occurs in the pharyngeal cross-sectional area. As such, changes in pharyngeal and/or laryngeal caliber as expiration progresses may possibly be used to determine airway patency for a subsequent inspiration. Further, some degree of diaphragm activation (e.g., including PNS, etc.) may allow for an examination of characteristics of airway patency, which, in turn, may be used to call for appropriate diaphragm activation.

With respect to aspects of PNS and upper airway characteristics, a report by Sériès et al., "Assessment of upper airway stabilizing forces with the use of phrenic nerve stimulation in conscious humans," *J Appl Physiol* 94: 2289-2295, (2003), states that "phrenic nerve stimulation (PNS) applied at end-expiration allows the investigation of passive upper airway (UA) dynamic during wakefulness". The report also found that the percentage of flow-limited twitches was significantly higher when applied phrenic nerve stimulation was delivered during expiration than during inspiration, which led to the conclusion that upper airway dynamics are "significantly influenced by the inspiratory/expiratory timing at which PNS is applied". The report by Sériès et al. is incorporated by reference herein.

One aspect of an exemplary approach disclosed herein aims to disassociate phasic activation of upper airway muscles and respiratory muscles that drive inspiration. Another aspect of such an exemplary approach optionally aims to characterize upper airway characteristics based at least in part on upper airway dynamics observed from expiratory to inspiratory parts of the respiratory cycle, with or without calling for or applying diaphragm activation.

Figure 4:
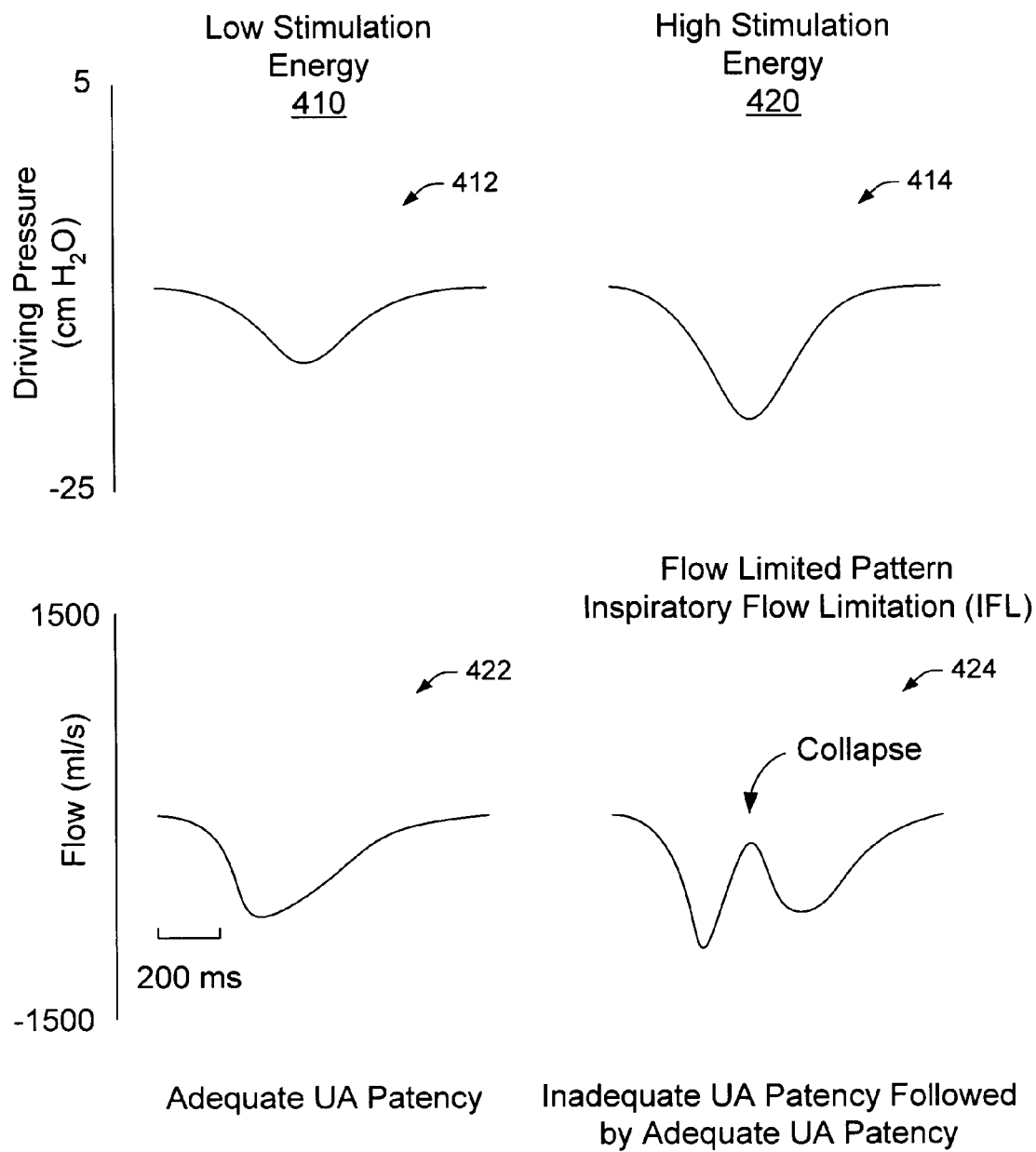
FIG. 4 is a series of plots of respiratory behavior for an instance of no flow limitation and for an instance of flow limitation in response to artificial diaphragm activation.

FIG. 4 shows exemplary inspiratory data 400 in two sets of plots 410, 420 that correspond to artificial diaphragm activation. One set 410 corresponds to low energy PNS delivered at the end of an expiratory part of a respiratory cycle while the other set 420 corresponds to high energy PNS delivered at the end of an expiratory part of a respiratory cycle. With respect to driving pressure with respect to time 412, 422, the high energy stimulation results in a higher driving pressure when compared to the low energy stimulation. As shown by data in the flow plots 414, 424, the higher driving pressure exceeds a critical pressure of the airway and, hence, the airway collapses. While the airway flow recovers shortly thereafter, in some instances, it may be advisable to avoid artificial diaphragm activation that can result in airway collapse. For example, patients having cardiac heart failure (e.g., NYHA classes III or IV) may not tolerate severe airway collapses, high energy stimulation that results in collapse unnecessarily wastes stimulation power, and some patients may have adverse physical and/or psychological reactions to airway collapse.

Figure 5:
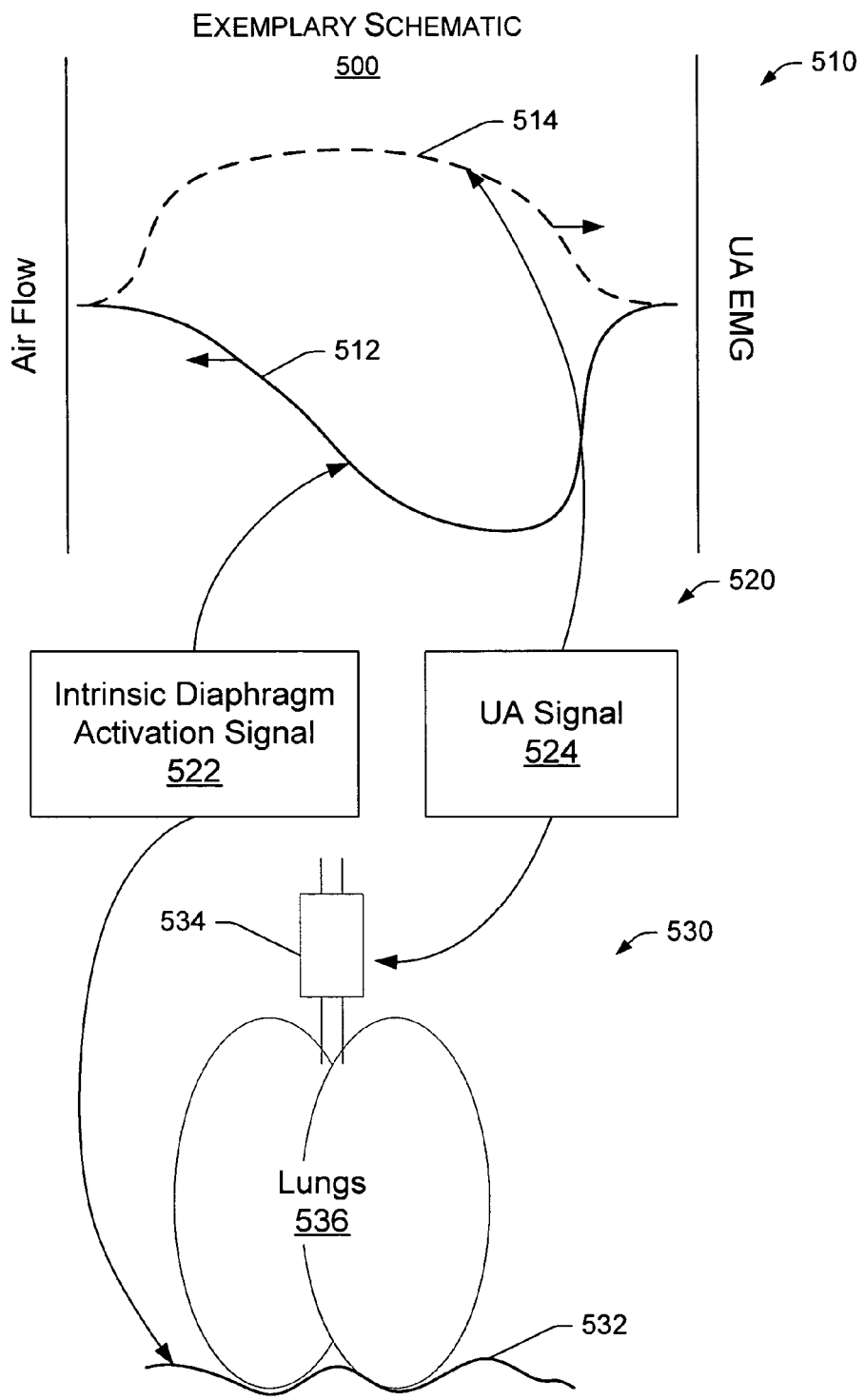
FIG. 5 is a schematic that includes a plot, signal generators and an approximate physiologic diagram for intrinsic inspiration.

FIG. 5 shows an exemplary schematic 500 that includes a plot 510, signal generators 520 and an approximate physiological respiration system 530. In the schematic 500, the signal generators 520 include an intrinsic diaphragm activation signal generator 522 and an upper airway muscle signal generator 524 that correspond to physiological generators primarily located in the brain. The intrinsic diaphragm activation signal generator 522 generates, for example, an intrinsic phrenic nerve stimulation signal that causes contraction of the diaphragm 532. The upper airway signal generator 524 generates an intrinsic upper airway signal that causes contraction of muscles in the upper airway 534.

The plot 510 depicts exemplary measurable signals indicative of intrinsic diaphragm activation and intrinsic upper airway muscle activation. The left side ordinate corresponds to data for air flow (e.g., ml/s) 512, measured as a negative value for air flow to the lungs. The right side ordinate corresponds to data for electrical activity of upper airway muscles 514 as recorded, for example, by an electromyography (EMG). In normal respiration, some degree of coordination exists between the intrinsic diaphragm signal generator 522 and the upper airway muscle signal generator 524. For example, the peak in flow occurs only after significant upper airway muscle activity. Thus, in the schematic 500, a relationship exists between flow and upper airway muscle tone whereby the upper airway muscle tone is sufficient to handle negative pressures generated by diaphragm activation.

Studies have shown that, in general, upper airway dilator muscles are activated before inspiratory muscles, with peak upper airway EMG activity being reached before peak activity of the diaphragm. Thus, some degree of pre-activation can allow for stabilization of upper airway structures for inspiratory flow and a decrease in work of breathing by decreasing upper airway resistance. Further, studies indicate that PNS does not cause a rise in upper airway genioglossus (GG) EMG activity until the maximal driving pressure has been reached (see, e.g., Sériès et al., "Influence of genioglossus tonic activity on upper airway dynamics assessed by phrenic nerve stimulation", *J Appl Physiol* 92: 418-423, (2002), which is incorporated by reference herein). Thus, artificial diaphragm activation alone cannot be expected to increase upper airway muscle tone. As described further below, various exemplary mechanisms call for diaphragm activation only when adequate upper airway muscle tone exists or may be expected to exist.

Figure 6:
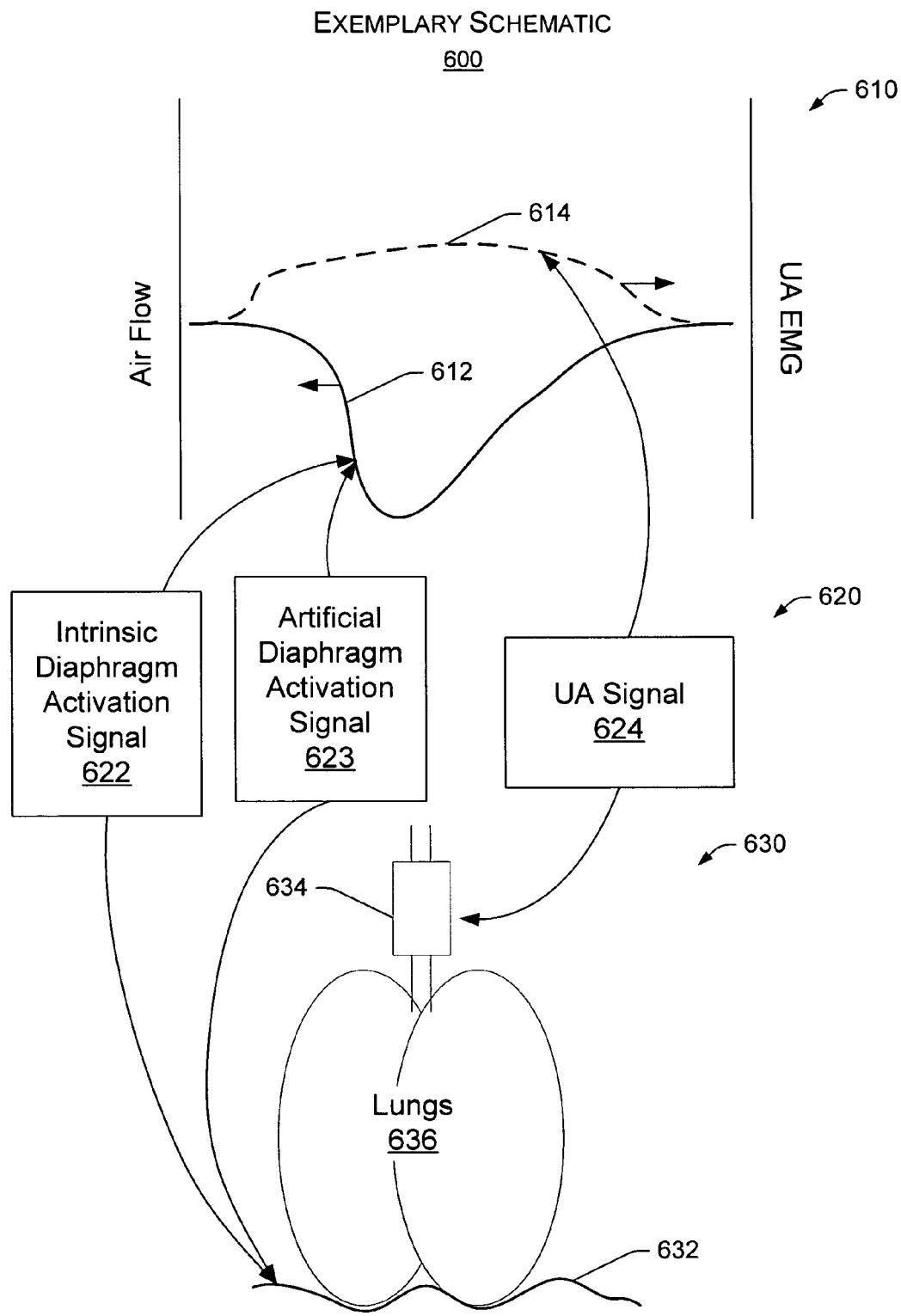
FIG. 6 is a schematic that includes a plot, signal generators and an approximate physiologic diagram for inspiration responsive to artificial diaphragm activation and some degree of intrinsic respiration.

FIG. 6 shows an exemplary schematic 600 that includes a plot 610, signal generators 620 and an approximate physiological respiration system 630. In the schematic 600, the signal generators 620 include an intrinsic diaphragm activation signal 622 that corresponds to a physiological generator primarily located in the brain, an artificial diaphragm activation signal generator 623 that corresponds at least in part to, for example, an implantable stimulation device, and an upper airway muscle signal generator 624 that corresponds to a physiological generator primarily located in the brain. The artificial diaphragm activation signal generator 623 generates, for example, a PNS signal that causes contraction of the diaphragm 632. The upper airway signal generator 624 generates an intrinsic upper airway signal that causes contraction of muscles in the upper airway 634. As described herein, any problem with the intrinsic diaphragm activation signal generator 622 may cause generation of a signal by the artificial diaphragm activation signal generator 623.

The plot 610 depicts exemplary measurable signals indicative of artificial diaphragm activation and optionally intrinsic diaphragm activation and upper airway muscle stimulation. The left side ordinate corresponds to data for air flow (e.g., ml/s) 612, measured as a negative value for air flow to the lungs. The right side ordinate corresponds to data for electrical activity of upper airway muscles 614 as recorded, for example, by an electromyography (EMG). While in normal respiration, some degree of coordination exists between an intrinsic phrenic nerve signal generator and an intrinsic upper airway muscle signal generator, in applied respiratory therapy (e.g., to a phrenic nerve), coordination must typically occur by other means.

In the plot 610, the flow data 612 correspond to respiration that has some underlying level of intrinsic respiration. For example, the presence of some level of UA EMG generally indicates that at least some intrinsic respiration is present. The flow pattern exhibited by the flow data 612 are indicative of typical augmented respiration (e.g., via artificial diaphragm activation) where flow limitation (e.g., upper airway collapse) has not occurred. One reason for the lack of flow limitation may be the presence of sufficient upper airway tone as exhibited by the EMG data 614. In this example, if sufficient tone was not present, then one may expect a flow pattern such as the flow pattern exhibited by the data 424 of FIG. 4.

Various exemplary mechanisms described herein optionally account for upper airway tone (e.g., measured via a pressure, stress and/or strain sensor, etc.), upper airway signal generation (e.g., measured via a nerve activity sensor, etc.), upper airway muscle activity (e.g., measured via EMG, etc.), flow (e.g., measured via a flow and/or pressure sensor, etc.), and/or chest volume, movement and/or position (e.g., measured via an impedance sensor, etc.). Such factors allow for artificial diaphragm activation in a manner that has a reduced risk of upper airway collapse. In addition, such factors may be used to determine critical parameters for use in predicting conditions where upper airway collapse may occur.

With respect to artificial diaphragm activation, call for activation and/or delivery of stimulation aimed at activation are typically synchronized with an intrinsic respiration signal or associated physiological signal and, in particular, an inspiratory phase of respiration. Further, stimulation power (e.g., energy delivered over time) is typically proportional to a level of intrinsic inspiratory drive and/or a measure of upper airway patency (e.g., noting that inspiratory drive may infer upper airway patency). While signals and sensing intrinsic inspiratory drive and/or upper airway patency have been discussed elsewhere herein such signals and sensing thereof optionally include impedance, pressure, photoplethysmography, IEGM, nerve sensing, respiratory sinus arrhythmia, etc. Photoplethysmography relies on emission and detection of radiation and may detect levels of components in blood, thickness of tissue per a given area, etc. A photoplethysmography sensor may be positioned subcutaneously, transcutaneously, superficially, etc.

With respect to IEGM information, respiration may be inferred by respiratory sinus arrhythmia and/or other indicia. For example, a report by de Chazal et al., "Automated processing of the single-lead electrocardiogram for the detection of obstructive sleep apnoea", *IEEE Trans Biomed Eng,* 50 (6): 686-96 (2003), included a method for detection of obstructive apnoea using nighttime single-lead ECG recordings. Results of the study indicated that normal recordings could be separated from apnoea recordings with a high success rate and a high minute-by-minute classification accuracy. The report by de Chazal et al. is incorporated by reference herein.

With respect to artificial diaphragm activation parameters, one parameter may be pulse width of a stimulation pulse. In general, where diaphragm activation is achieved via phrenic nerve and/or diaphragm muscle stimulation, a pulse width may be as short as approximately 10 microseconds to as long as a millisecond. Other values may be used where appropriate. Regarding potential for PNS, stimulation may be delivered using a potential in a range from approximately 0.1 V to approximately 10 V. Other parameters such as duty cycle, duty, total energy, power, electrode configuration, polarity, pulse train shape, pulse train length, pulse frequency, etc. may be adjusted to achieve appropriate diaphragm activation. In general, power is determined based on energy delivered over a period of time. As described herein, a change in power may occur due to a change in pulse width, number of pulses, etc.; whereas, a change in energy typically refers to a change in energy for a given period of time. For example, a 30 microsecond pulse using a potential of 4 V will deliver an energy level different than a 30 microsecond pulse using a potential of 8 V, wherein delivery occurs over substantially the same resistance.

Figure 7:
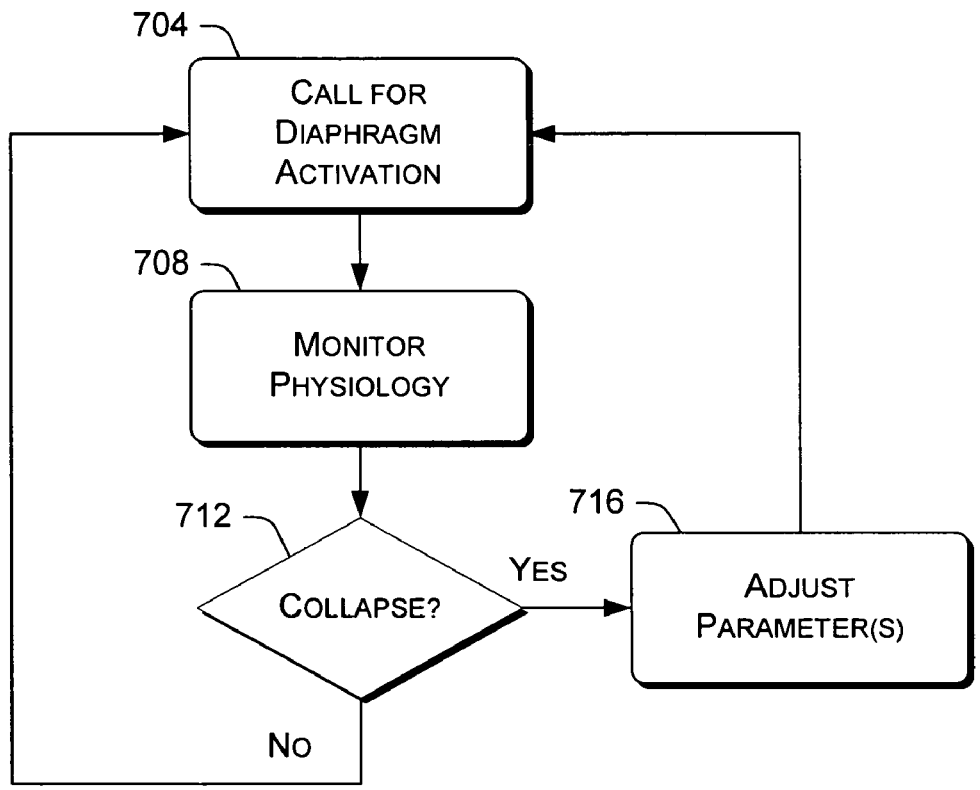
FIG. 7 is a block diagram of an exemplary method for monitoring respiratory activity and adjusting one or more parameters for diaphragm activation in response to activity indicative of upper airway collapse or risk of collapse.

FIG. 7 shows an exemplary method 700 that calls for artificial diaphragm activation. In a call block 704, a call is made for some form of artificial diaphragm activation. For example, phrenic nerve stimulation may be applied to a patient's diaphragm and/or phrenic nerve (e.g., right and/or left phrenic nerve, etc.). Before, during and/or after the call for activation, a monitor block 708 monitors the patient's respiration. The monitor block 708 optionally uses one or more sensors to monitor chest characteristics. Information acquired or sensed during monitoring is then used in a decision block 712 that decides if collapse is occurring or optionally whether a significant risk of collapse exists, etc. If the decision block 712 decides that collapse is occurring, then the method 700 continues in an adjustment block 716 wherein one or more activation parameters are adjusted. Thereafter, if appropriate, the method 700 continues in the call block 704. If the decision block 712 decides that collapse is not occurring, then the exemplary method 700 continues in the call block 704, as appropriate.

With respect to the call block 704, a call for diaphragm activation may occur according to occurrence of any of a variety of events related to oscillations characteristic of CSR. For example, if sensed information indicates that a patient's respiration is oscillating between hyperpnea and hypopnea (e.g., within a range of CSR like periodicity, etc.), then the call block 704 may call for diaphragm activation to occur during any part of a decrescendo and/or crescendo. Further, as described further below, a call may be in response to inadequate respiration as determined by one or more limits, etc.

Referring to the plots 400 of FIG. 4, an exemplary method optionally calls for diaphragm activation and monitors physiology indicative of upper airway patency. Such a method may determine upper airway patency as a function of energy or power delivered for diaphragm activation or one or more other suitable parameters associated with diaphragm activation, respiration, cardiac function, etc. Accordingly, in this example, a parameter adjustment block or other suitable block may operate to store parameters or to update a model that relates to upper airway patency. A model may rely on input of one or more measured or programmed values and in turn limit diaphragm activation energy or power in a manner that reduces risk of upper airway collapse.

While a patient may be able to tolerate an airway collapse in response to artificial and/or intrinsic diaphragm activation, energy consumed in artificial diaphragm activation can unnecessarily deplete stored energy of an implanted stimulation device. Thus, for at least this reason, situations that cause upper airway collapse may be avoided. Of course, where an exemplary method aims to determine airway patency as a function of stimulation energy, power and/or timing of stimulation, then such an expenditure of stored energy may be acceptable. Such an exemplary method may be used to determine stimulation energy or power delivered for diaphragm activation and/or timing of stimulation.

Figure 8:
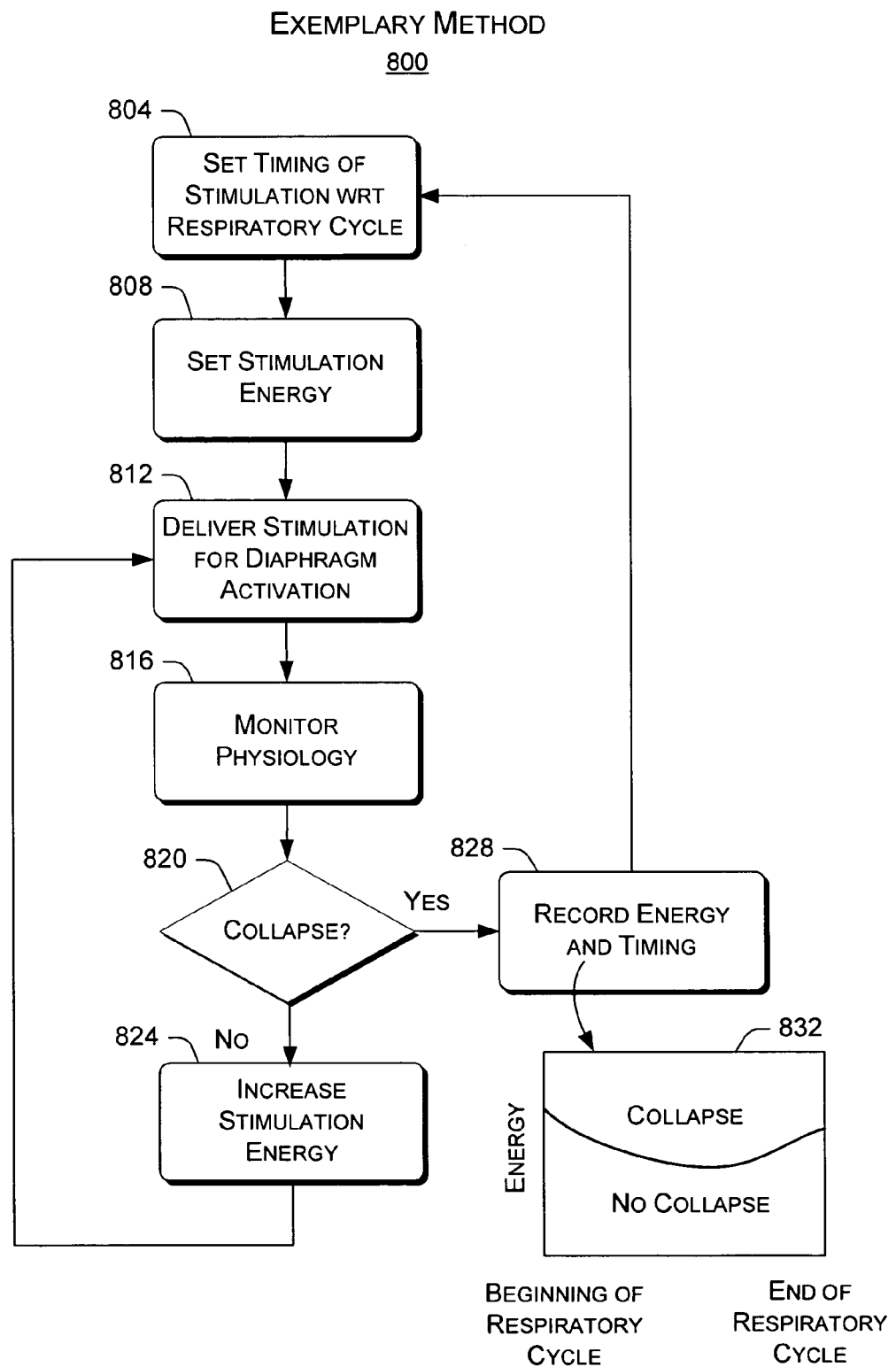
FIG. 8 is a block diagram of an exemplary method for monitoring respiratory activity and determining when an upper airway collapse may occur for giving timings and/or stimulation energies.

Referring to the plot 510 of FIG. 5 and the plot 610 of FIG. 6, upper airway activity typically precedes flow. Thus, at the onset of intrinsically triggered flow, it is likely that at least some degree of natural upper airway activity exists. Thus, an exemplary method triggers applied phrenic nerve stimulation only after or upon detection of intrinsically triggered flow. Of course, other possibilities exist. FIG. 8 shows an exemplary method 800 for determining stimulation energy or power versus respiratory cycle time. In general, such a method is implemented during normal respiration unaffected by CSR.

The exemplary method 800 commences in a set timing block 804 that sets a time with respect to a respiratory cycle to commence delivery of stimulation energy to cause diaphragm activation. For example, if respiration is normal and relatively steady in frequency, then the set block 804 may set a time as a percentage or fraction of the respiratory cycle. In this example, a set stimulation energy block 808 follows that sets stimulation energy to be delivered. A delivery block 812 then delivers the stimulation energy for diaphragm activation according to the timing set in the set timing block 804. A monitor block 816 follows, which may be active throughout implementation of the exemplary method 800. The monitor block 816 monitors physiology that can indicate whether an airway collapse is occurring or has occurred. A decision block 820 relies on such information to decide if a collapse occurred in response to the delivered stimulation at the energy level and timing set by the appropriate block 804, 808. If a collapse did not occur, then the method 800 continues in an increase stimulation energy block 824 that increases the stimulation energy. Thereafter, the method 800 continues at the delivery block 812.

However, if the decision block 820 decides that a collapse occurred, then a record block 828 records the energy and the associated timing. Thereafter, the method 800 optionally continues at the set timing block 804 whereby other stimulation timings and/or energies may be investigated. An exemplary plot 832 of stimulation energy versus respiratory cycle timing includes a hypothetical line based on, for example, recorded information. The exemplary plot 832 includes an upper portion above the line that indicates collapse is likely to occur for stimulation energies with respective timings whereas a lower portion below the line indicates that collapse is not likely to occur for stimulation energies with respective timings. Such a plot or recorded information may infer or allow for a determination of airway patency at various times in a respiratory cycle. Such information is optionally used to determine timings and/or energies of stimulation aimed at terminating CSR. For example, an exemplary method may use a particular timing to commence delivery of a stimulation energy wherein the energy is proportional to a level of intrinsic activity related to diaphragm activation.

The exemplary plot 832 may be extended in one or more dimensions to include, for example, tidal volume, power, flow, etc. Tidal volume with respect to energy and with respect to collapse may allow for enhanced control and treatment of respiratory issues. In general, the exemplary method 800 may rely on power and/or energy where appropriate.

Figure 9:
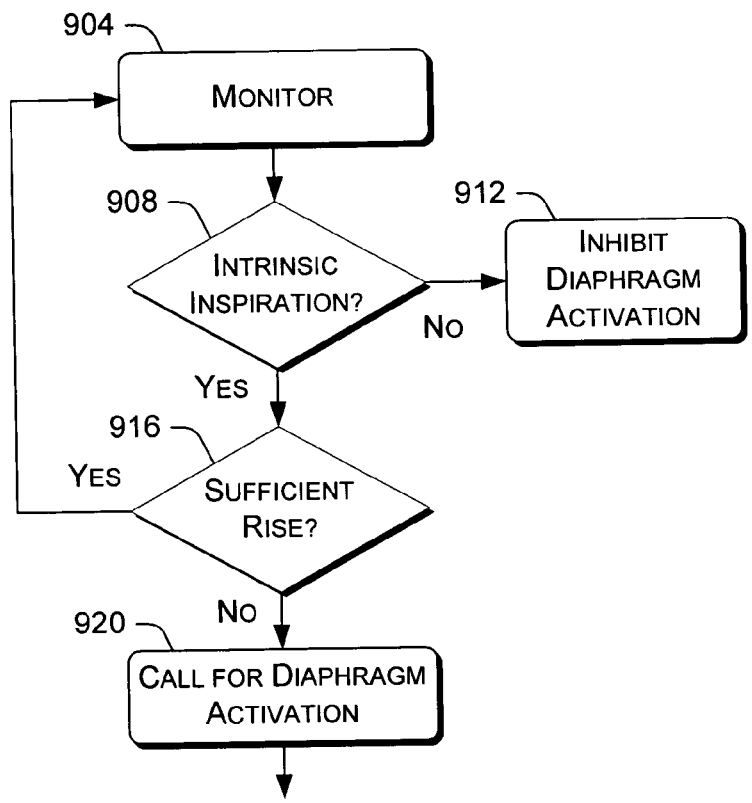
FIG. 9 is a block diagram of an exemplary method for monitoring respiratory activity and delivering applied stimulation in response to activity indicative of a sufficient inspiratory drive.

With respect to calling for artificial diaphragm activation in response to oscillations or a decrescendo and/or crescendo characteristic CSR, FIG. 9 shows an exemplary method 900 that aims to terminate such oscillations or decrescendo or crescendo. The exemplary method 900 may be implemented after detection of oscillations characteristic of CSR.

The exemplary method 900 includes a monitor block 904 wherein activity is monitored for information that can indicate whether intrinsic inspiration is present. A decision block 908 follows that decides, for example, on the basis of monitored characteristics, whether intrinsic inspiration is present. If the decision block 908 decides that intrinsic inspiration is not present, then the method 900 continues in an inhibition block 912 that inhibits delivery of diaphragm activation. If the decision block 908 decides that intrinsic inspiration is present then the method 900 may call for artificial diaphragm activation in the call block 920. However, as shown in the exemplary method 900, an optional subsequent decision block 916 decides whether the intrinsic inspiration has a sufficient rise or other indicia that may be used to determine if the intrinsic inspiratory activity is sufficient. If the decision block 916 decides that the intrinsic inspiration is sufficient so as to not require therapy, then the method 900 continues in the monitor block 904. If the decision block 916 decides that the rise is not sufficient, then the method continues in the call block 920, which calls for diaphragm activation. Thereafter, the method 900 optionally continues in a block (e.g., the monitor block 708) of the method 700 of FIG. 7. When combined with aspects of the method 700, the method 900 may adjust to or otherwise account for upper airway collapse.

The exemplary method 900 may rely on a sensor (e.g., impedance, etc.) that can determine onset of intrinsic inspiration and integrate, time derivate, etc., the sensed information to determine whether intrinsic inspiration could benefit from augmentation.

As already mentioned, various exemplary mechanisms (e.g., suitably implemented as or in methods, devices, systems, etc.) aim to treat issues associated with Cheyne-Stokes respiration (CSR). CSR is typically characterized by alternating periods of hypopnea or apnea and hyperpnea wherein, for example, over a period of about 1 minute, an episode of about 10 to about 20 seconds of apnea or hypopnea may be observed followed by respirations of increasing depth and perhaps frequency. While frequency information may be used, an exemplary mechanism may rely predominantly on an amplitude measure. Further, CSR often repeats, thus, there may be a characteristic repetition cycle associated with CSR. Knowledge of repetition may be gained through sensing and/or other means (e.g., patient monitoring, follow-up, etc.) and may be used in determining when to call for artificial diaphragm activation.

Figure 10:
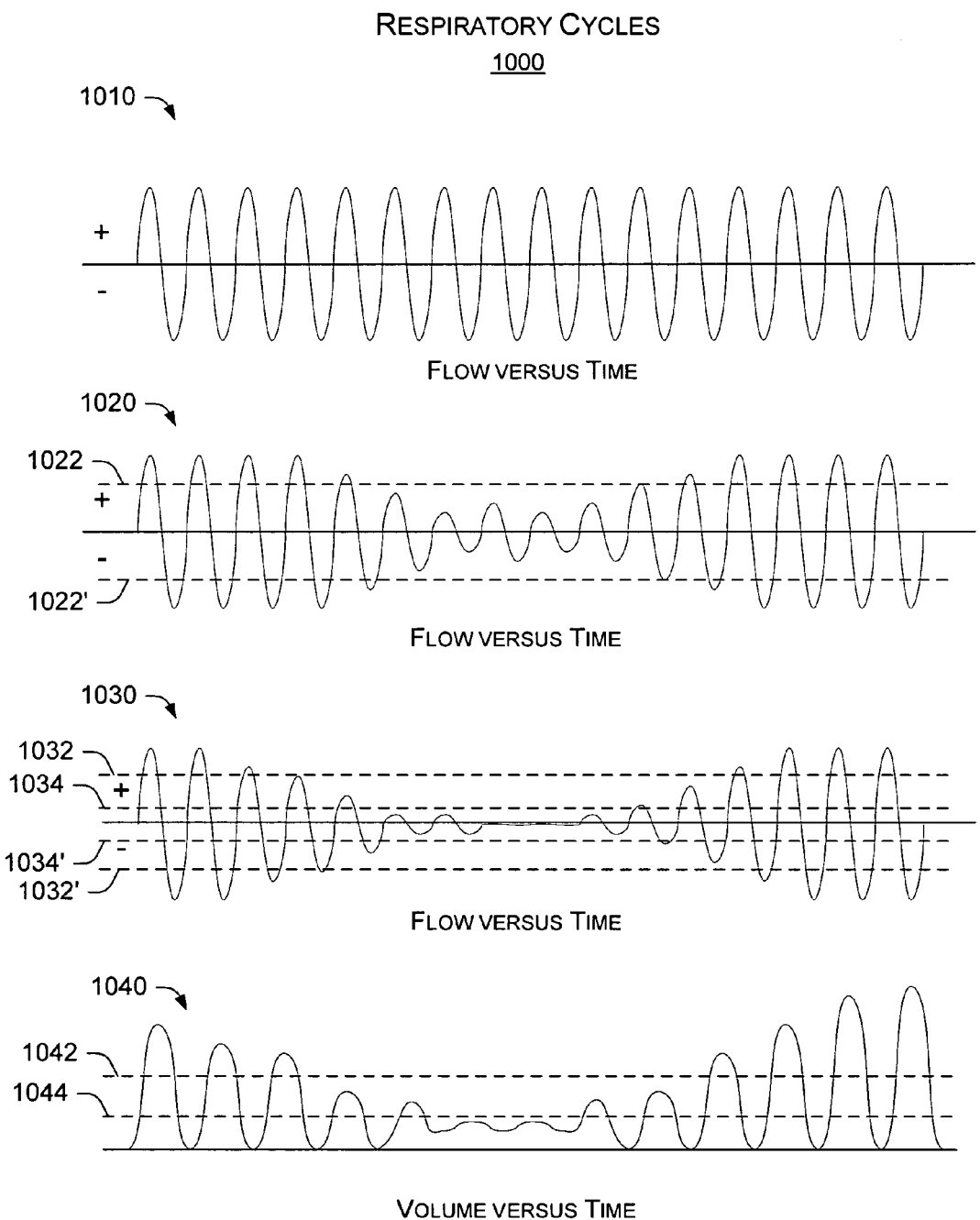
FIG. 10 is a series of plots showing various respiratory cycle types including normal, Cheyne-Stokes respiration and Cheyne-Stokes respiration where in a middle section of the two lower plots respiration is reduced to approximately zero.

FIG. 10 shows various respiratory cycle plots 1000 where for three of the plots 1010, 1020 and 1030 a positive deviation (+) represents flow from the lungs (expiration) and a negative deviation (−) represents flow to the lungs (inspiration). Thus, according to these three plots the horizontal centerline represents a point where there is no flow. In general, inspiration increases steadily to a maximum air flow, which then decreases as the tidal volume for the particular inspiration is reached. Correspondingly, expiration increases steadily to a maximum expiration air flow, which then decreases as the tidal volume is expired. While some plots indicate various actions with respect to a maximum in air flow, others may indicate actions with respect to volume of air (e.g., tidal volume, etc.). A fourth plot 1040 shows essentially the same information as presented in the third plot 1030 but as volume with respect to time instead of air flow with respect to time. In general, volume and air flow may be ascertained from information presented in the plots 1010, 1020, 1030 and 1040.

The first and uppermost plot 1010 shows a regular respiratory cycle with substantially constant and even inspiratory and expiratory phases. A regular respiratory cycle typically requires no augmentation of intrinsic phrenic nerve stimulation (e.g., indirect and/or direct phrenic nerve and/or diaphragm stimulation). The second plot 1020 exhibits an abnormal respiratory cycle pattern. In particular, the plot 1020 exhibits diminishing flow followed by increasing flow, for example, a decrescendo followed by a crescendo. A central region of the plot 1020 exhibits flow that does not exceed an expiratory flow limit 1022 and that does not exceed an inspiratory flow limit 1022'. One or more flow limits may be used to initiate a control algorithm that calls for artificial diaphragm stimulation.

The third plot 1030 exhibits another abnormal respiratory cycle pattern. In particular, the plot 1030 exhibits diminishing flow followed by essentially no flow followed by increasing flow, for example, a decrescendo followed by essentially no flow followed by a crescendo. The plot 1030 includes various limits including an high expiratory flow limit 1032, a low expiratory flow limit 1034, a low inspiratory flow limit 1034' and a high inspiratory flow limit 1032'. According to the low limits 1034, 1034', such limits may be used to terminate any call for or delivery of artificial diaphragm activation. For example, such limits may indicate that upper airway muscle tone is insufficient to support pressures associated with certain applied phrenic nerve stimulation or diaphragm stimulation.

The fourth and lowermost plot 1040 exhibits another abnormal respiratory cycle pattern. In particular, the plot 1040 exhibits diminishing tidal volume followed by essentially no tidal volume followed by increasing tidal volume, for example, a decrescendo in total volume followed by essentially no volume or flow followed by a crescendo in total volume. The plot 1040 includes various limits including a total volume limit 1042 and a low volume limit 1044. Accordingly the low limit 1044 may be used to terminate any call for or delivery of artificial diaphragm activation. For example, such limits may indicate that upper airway muscle tone is insufficient to support pressures associated with certain applied phrenic nerve stimulation or diaphragm stimulation.

Figure 11:
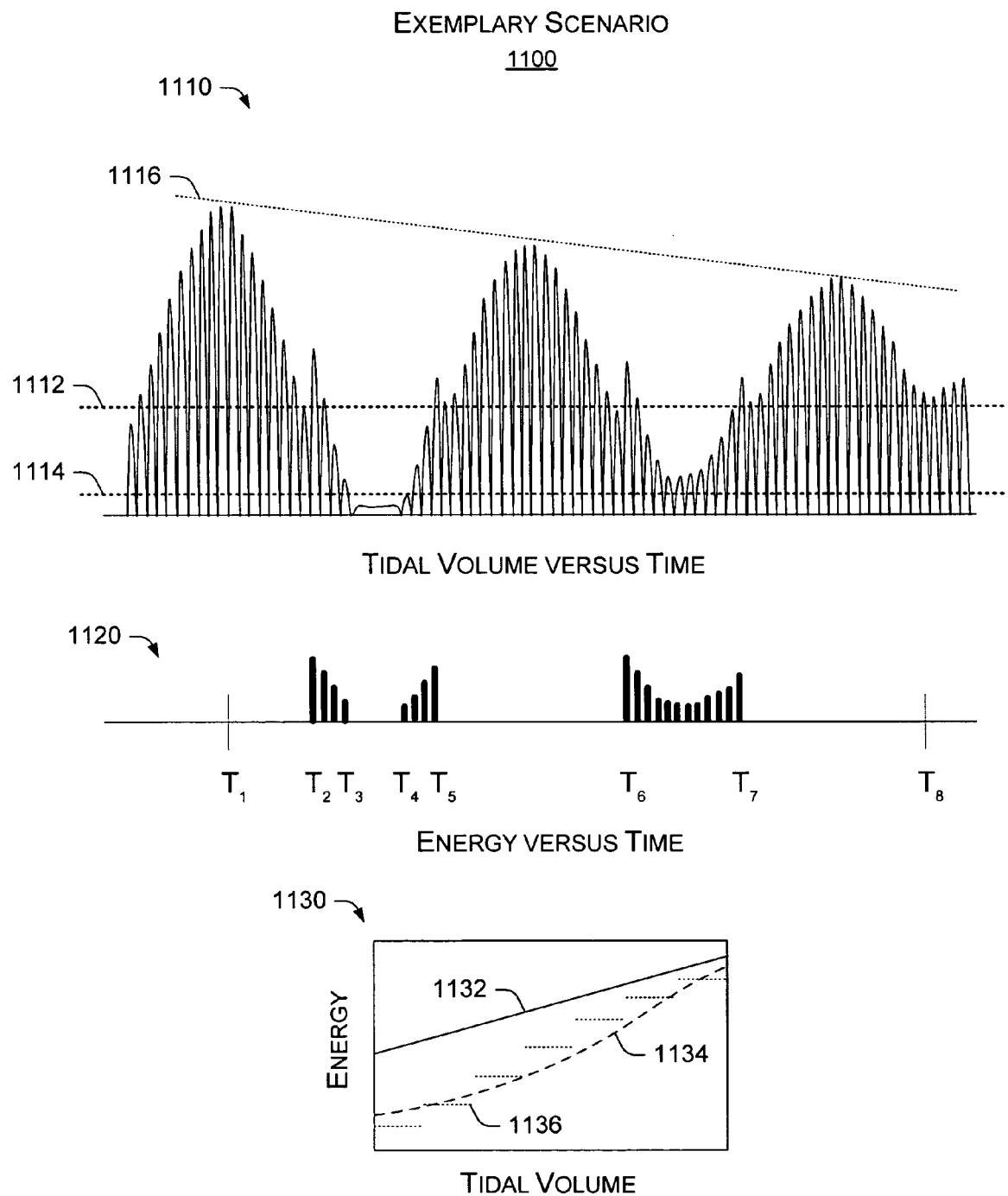
FIG. 11 is diagram of an exemplary scenario wherein oscillation amplitude diminishes in response to diaphragm activation.

FIG. 11 shows an exemplary scenario 1100 wherein an exemplary method calls for delivery of stimulation energy or power for diaphragm activation. The scenario 1100 includes a plot of tidal volume versus time 1110, a plot of energy versus time 1120 and a plot of energy versus tidal volume 1130. The plot of tidal volume versus time 1110 exhibits oscillatory behavior characteristic of CSR. The plot of energy versus time 1120 shows short pulses at a relatively constant energy level. Of course, other types of pulses or pulse trains may be used to achieve a certain total energy or power. At a time $T_1$, a determination is made that oscillations exist or that a patient is experiencing CSR. In response to this determination, control logic calls for delivery of stimulation energy for diaphragm activation when tidal volume falls below a certain level 1112. At a time $T_2$, as the tidal volume falls as part of the oscillatory behavior, the call for delivery of stimulation energy results in delivery of stimulation energy that causes an increase in tidal volume. In this example, stimulation energy varies with respect to tidal volume. In particular, the stimulation energy decreases as tidal volume decreases and increases as tidal volume increases.

The plot 1130 includes various relationships between energy or power and tidal volume. A linear relationship 1132 indicates that energy is linearly proportional to tidal volume and may include an offset typical of a linear equation. A nonlinear relationship 1134 indicates that energy is nonlinear with respect to tidal volume. Such a relationship may be nonlinearly proportional. A step-wise relationship 1136 indicates that energy changes in one or more discrete steps with respect to tidal volume (e.g., energy or power may remain constant over a certain range of tidal volume). As already mentioned, proportional includes linearly, nonlinearly and/or step-wise proportional. The various relationships 1132, 1134, 1136 of the plot 1130 are nondecreasing monotonic with respect to increasing tidal volume. Of course, other relationships may be possible, including those that are not nondecreasing monotonic with respect to increasing tidal volume. In general, a plot such as the plot 1130 may be independent of time. Other plots or relationships between energy or power and a respiration parameter may depend on time. In particular, a predictive model may rely on a time variable to predict future tidal volume or appropriate energy or power.

In the scenario 1100, at a time $T_3$, however, a second limit 1114 acts to inhibit calling for or delivery of stimulation energy for diaphragm activation when tidal volume or flow falls below the limit 1114. The second limit 1114 may be implemented when change in a variable related to respiration indicates that respiration has essentially ceased. For example, if a patient enters apnea, then there may be insufficient airway patency to support any meaningful diaphragm activation. As such, inhibition of delivery acts to conserve energy of an implantable stimulation device.

At a time $T_4$, the tidal volume rises above the second limit 1114 and again, stimulation energy is delivered in an effort to increase tidal volume. At a time $T_5$, the tidal volume, as assisted by delivery of stimulation energy for diaphragm stimulation, rises above the first limit 1112. Consequently, no call is made for delivery of stimulation energy for diaphragm stimulation. At a time $T_6$, however, tidal volume falls below the limit 1112, which results in a call for and delivery of stimulation energy for diaphragm activation. From time $T_6$ to a time $T_7$, the tidal volume remains above the limit 1104 and hence calls for stimulation continue until tidal volume exceeds the limit 1112.

In the scenario 1100, a line 1116 approximates a decrease in oscillatory behavior over time as a consequence of the delivered stimulation energy. Thus, in this scenario 1100, the exemplary method generally acts to break or terminate oscillations or CSR over a period of time or oscillatory cycles. In particular, control occurs during phases of shallow breathing, which in turn diminish tidal volume extreme during phases of deep breathing. While the scenario 1100 shows respiration of somewhat regular frequency and varying in breath depth, the exemplary method may apply to scenarios where respiratory frequency varies significantly. In general, the exemplary method implemented in the scenario 1100 dampens oscillations in respiration (e.g., tidal volume, flow, etc.).

Figure 12:
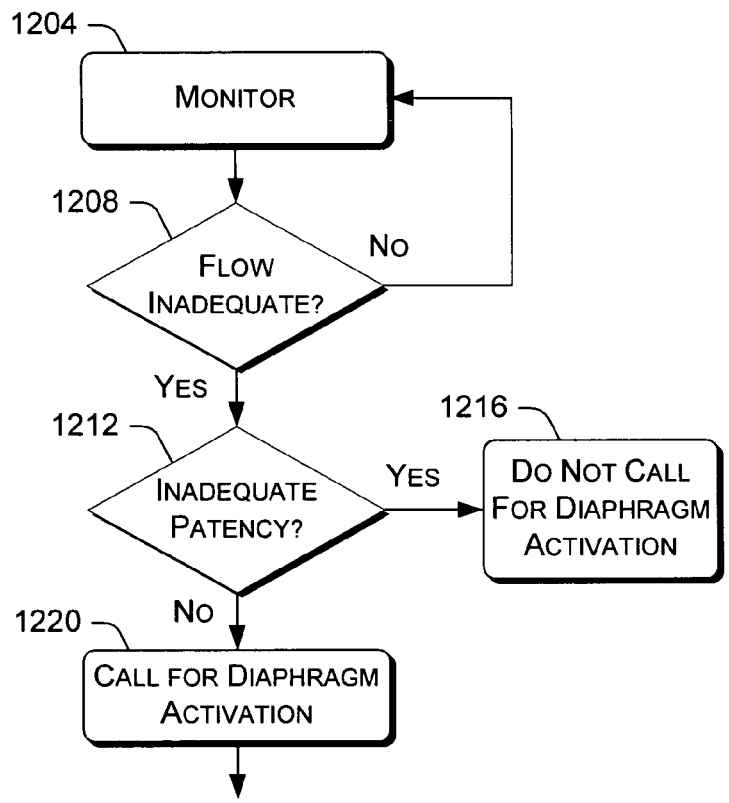
FIG. 12 is a block diagram of an exemplary method for monitoring respiratory activity and calling for diaphragm activation in response to flow adequacy and activity indicative of sufficient upper airway patency.

FIG. 12 shows an exemplary method 1200 for determining whether to call for artificial diaphragm activation. A monitor block 1204 monitors activity related respiration, for example, related to expiratory and/or inspiratory flow. A decision block 1208 follows that decides, based at least in part on the information, whether the inspiratory and/or expiratory flow are adequate. If the flow is adequate, then the method 1200 continues in the monitor block 1204; however, if the flow is inadequate (i.e., could benefit from augmentation), then another decision block 1212 follows which decides if the information indicates that upper airway patency may be inadequate for a prospective stimulation therapy (e.g., phrenic nerve, diaphragm, etc.) for increasing respiratory flow. If the decision block 1212 decides that upper airway patency is inadequate (or likely to be inadequate), then in a do not call block 1216, the method 1200 ensures that a call is not made for delivery of artificial diaphragm activation. As an alternative or in addition to, the method 1200 may enter a delivery block 1216 that aims to deliver appropriate therapy such as pacing and/or other stimulation therapy that may cause an increase in upper airway patency. Thereafter, a call for artificial diaphragm activation may occur.

In the instance that the decision block 1212 decides that upper airway patency is adequate then the method 1200 continues in a call block 1220 that calls for artificial diaphragm activation. The artificial diaphragm activation may be called for and delivered at a stimulation energy or power that is proportional to an indicator of airway patency and/or based on a nondecreasing monotonic relationship with respect to increasing airway patency. For example, the call block 1220 may call for use of a stimulation energy or power that is based at least in part on a tidal volume, air flow, or other respiratory characteristic that may indicate or be associated with a certain level of airway patency. For example, stimulation energy or power may be proportional to and/or based on a nondecreasing monotonic relationship with respect to increasing tidal volume, air flow, or other respiratory characteristic. The method 1200 optionally continues in a block (e.g., the monitor block 708) of the exemplary method 700 of FIG. 7.

Various exemplary methods, devices and/or systems deliver stimulation for artificial diaphragm activation in a non-continuous manner. For example, an exemplary method may call for and deliver phrenic nerve stimulation, when appropriate, to every other respiratory cycle.

Figure 13:
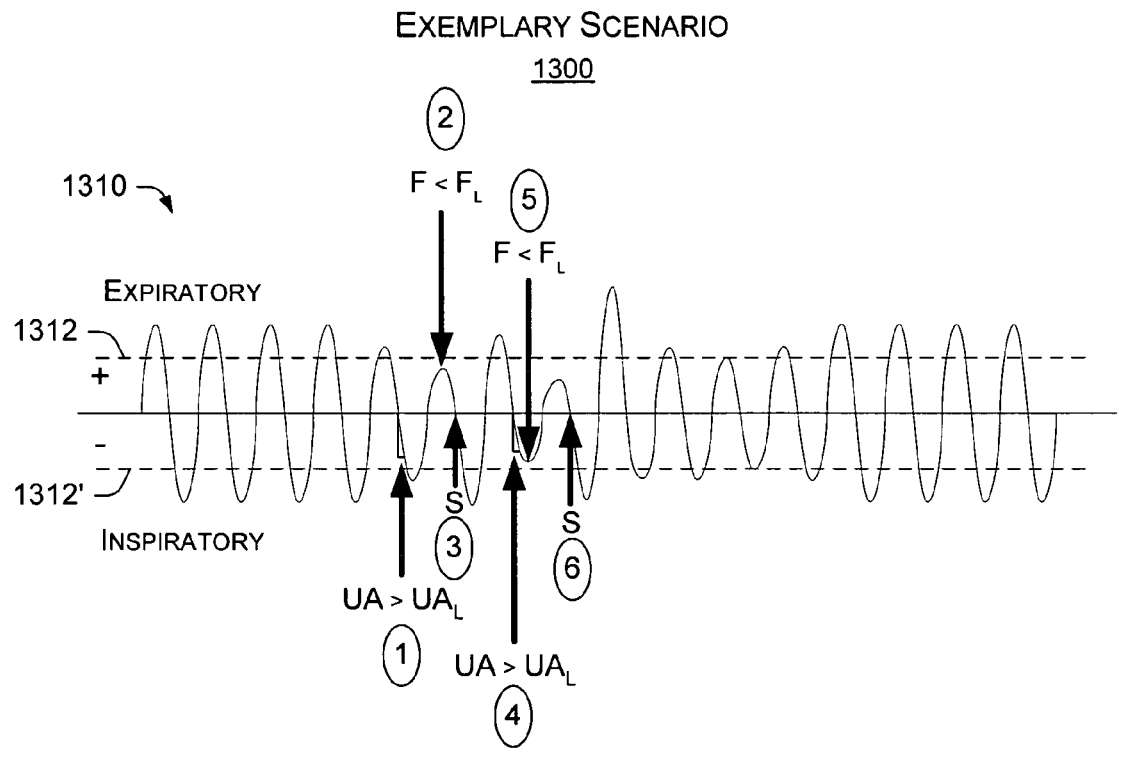
FIG. 13 is a diagram of an exemplary scenario that shows a respiratory pattern and prospective therapy responsive to respiratory characteristics in such a pattern.

FIG. 13 shows an exemplary scenario 1300 wherein augmentation of respiration occurs. The scenario 1300 includes a plot 1310 of exemplary data, for example, sensed via a sensor or monitor. An expiratory limit 1312 and an inspiratory limit 1312' indicate circumstances or conditions where artificial diaphragm activation may aid breathing. According to the scenario 1300, event 1 corresponds to sensing of indicia that indicate an adequate level of upper airway patency. The corresponding expiratory phase of the cycle exhibits a maximum air flow that is less than the expiratory limit 1312 (event 2). In response to the indicia of an adequate level of upper airway patency and an expiratory air flow that is less than the expiratory limit 1312, stimulation for artificial diaphragm activation is delivered that commences at approximately the end of the expiratory phase (event 3).

The energy or power level of any stimulation for diaphragm activation is optionally proportional to the upper airway patency and/or limited to reach a eupnic level (normal tidal volume level and/or normal air flow), the maximum expiratory flow and/or one or more other factors. For example, a power level may be determined at least in part by the following relationship:

$$P_s(t) = P_{Smax} * |dF_I/dt(t-1)|/|dF_I/dt(\text{normal})| \quad (1)$$

wherein $P_s(t)$ is the applied power level at time t, $P_{Smax}$ is a maximum power level, $|dF_I/dt(t-1)|$ is the absolute value of the derivative of inspiratory flow with respect to time just after the onset of inspiration at a time t−1, which is prior to time t, and $|dF_I/dt(t-1)|$ is the absolute value of the derivative of inspiratory flow with respect to time at the onset of inspiration for normal inspiration (e.g., an average of normal inspirations, etc.). In this manner, $P_s(t)$ increases as $|dF_I/dt(t-1)|$ increases. Of course, in the exemplary scenario 1100, $P_s(t)$ depends on $|dF_I/dt(t-1)|$ for a prior time since an expiratory flow value indicated that augmentation of inspiratory flow may be appropriate.

Another exemplary relationship relies on the maximum flow. For example, the following relationship may be used to determine stimulation power level:

$$P_S(t) = P_{Smax} * F_{max}(t-1)/F_L \quad (2)$$

wherein $F_{max}(t-1)$ is the maximum flow for a prior respiratory cycle where the respiratory cycle commences on the onset of an inspiration and terminates on an end or cessation of an expiration and $F_L$ is a flow limit. Thus, $P_S(t)$ increases as $F_{max}$ increases. In this example, a higher $F_{max}$ may indicate a greater degree of upper airway patency and hence the ability for the airway to withstand a larger diaphragm contraction and air intake driving force.

Options for delivering stimulation for diaphragm activation because an inspiratory flow value indicates that flow is inadequate include delivering the stimulation during the immediate inspiratory phase or delaying the delivering until a subsequent inspiratory phase. For example, if stimulation is delivered on a subsequent inspiration, the scenario of events labeled 4, 5 and 6 may occur. Event 4 corresponds to determining that upper airway patency UA is above some upper airway patency limit $UA_L$. Event 5 corresponds to determining that inspiratory flow F is less than some inspiratory flow limit $F_L$. In response to the circumstances, a call is made for artificial diaphragm activation and appropriate stimulation is delivered, as represented by event 6. In this example, stimulation for diaphragm activation commences approximately at the end of the expiratory phase of the respiratory cycle or approximately at the beginning of the inspiratory phase of the next respiratory cycle. As shown, the stimulation of events 3 and 6 is sufficient to cause the inspiratory flow to exceed the inspiratory limit 1312' and for the corresponding expiratory flow to exceed the expiratory limit 1312. Of course, depending on one or more stimulation parameters, the inspiratory flow and/or the corresponding expiratory flow may not exceed such limits. Further, a method such as the method 700 may be used to terminate or inhibit stimulation, for example, if any signs of collapse are noted.

In another alternative, stimulation may occur for the current respiratory cycle. If an inspiratory flow value (e.g., rise, max, etc.) indicates that augmentation of inspiratory flow may be appropriate, then, for example, the power level may be determined at least in part by the following relationship:

$$P_S(t)=P_{Smax}*|dF_I/dt(t)|/|dF_I/dt(\text{normal})| \qquad (3)$$

where the power level at time t is determined at least in part on the basis of the flow rise with respect to time for the same respiratory cycle. Power level may depend on the value according to relationship of Eqn. 2 or another relationship.

Figure 14:
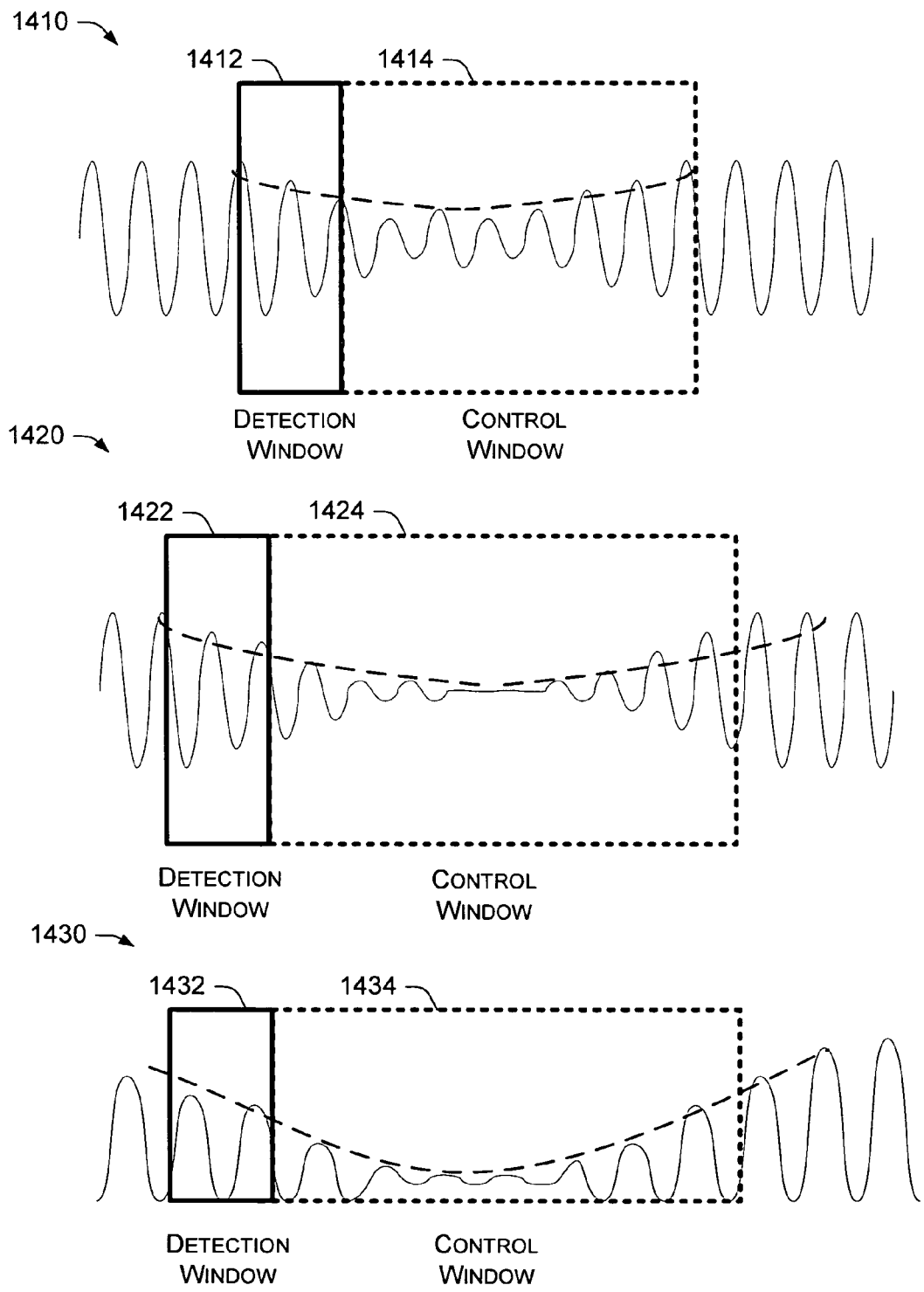
FIG. 14 is a series of plots of respiration wherein each plot shows predictive information, a detection window and a control window that may deliver therapy according to the predictive information.

FIG. 14 shows various exemplary schemes 1400 that rely on modeling respiratory behavior. For example, the scheme 1410 includes a region modeled by an exponential decay and an exponential rise that correspond to a decrescendo and a crescendo in respiratory flow. While an exponential relationship is shown, one or more other functions may be used to model respiratory behavior. The scheme 1420 also includes a region modeled by an exponential decay and an exponential rise that corresponds to a decrescendo and a crescendo in respiration; however, in the middle section of the region, respiratory flow decreases to approximately no flow.

Referring again to the scheme 1410, after modeling (e.g., input or acquired model, etc.), during a detection window 1412, a determination is made as to the nature of the respiratory cycle disturbance or abnormality. Based at least in part on information acquired in the detection window, a control scheme is implemented in an appropriate control window 1414. The particular scheme 1410 shows the control window only for reference, as the respiratory pattern shows no indication that stimulation for artificial diaphragm activity has been delivered.

If stimulation for diaphragm activation occurs during the control window 1414, such stimulation may occur throughout the window. In contrast, in the scheme 1420 (having detection window 1422 and control window 1424), the control may terminate where the expected intrinsic flow or upper airway patency falls below a certain level. For example, if the expected flow or patency falls below a level, then stimulation may be terminated because of a likelihood of upper airway collapse.

Another exemplary scheme 1430 includes various features of the scheme 1420; however, using information on volume with respect to time instead of flow with respect to time. Again, in general, information pertaining to flow or volume with respect to time is interchangeable through various operations using integrals, derivatives, etc.

In the exemplary schemes 1400, the energy or power level of stimulation for diaphragm activation may be proportional to the expected or modeled flow and/or based on a nondecreasing monotonic relationship with respect to increasing tidal volume, etc. In this manner, the stimulation may be proportional to expected intrinsic inspiratory activity and/or the expected upper airway patency.

Thus, various exemplary methods, devices and/or systems sense intrinsic respiration (e.g. as by an intrathoracic impedance signal) and whenever inspiration is determined to be reduced, call for or deliver stimulation for diaphragm activation at an energy or power level proportional to an intrinsic value or an estimate thereof. Of course energy or power may be based on a nondecreasing monotonic relationship with respect to increasing tidal volume, etc. Such stimulation may be delivered in a respiratory cycle associated with sensed information indicating a need or in a respiratory cycle subsequent to that associated with sensed information indicating a need for therapy. In various examples, a determination is optionally made as to whether respiratory information is indicative of CSR, which may, in turn, determine cycle length, frequency, etc., related to CSR.

Various exemplary methods, device and/or systems sense information indicative of thoracic volume. Such sensed information is optionally maintained as a running average of tidal volume on a breath by breath basis. For example, sensing of peak-to-peak amplitude of a respiratory component of intrathoracic impedance signal is acquired on a breath by breath basis and used to determine a running average tidal volume over a certain number of breaths (e.g., 5 breaths, etc.). More sophisticated (e.g., weighted, etc.) averages that specify a present running average that depends on tidal volumes of more recent breath(s) may also be employed. In another example, running average tidal volume represents a tidal volume of a prior breath, assuming the breath was not simply a sigh and that it was recorded without undue noise according to some degree of confidence and relevance. An exemplary implantable device may determine an average period of respiration or other respiratory cycle characteristics. Once an average period has been determined, an average interval between breaths is optionally maintained by stimulation delivered via an implanted device.

Under intrinsic control, if tidal volume of a breath falls below some threshold value of a running average tidal volume (e.g., 70%, etc.), a control algorithm may call for application of stimulation therapy to increase inspiration. In another example, if a spontaneous breath was not sensed in a given period of time, therapy is applied. The given period of time is optionally determined on the basis of a predicted respiratory period derived from an average respiratory period.

As described herein, therapy may include stimulation of a phrenic nerve and/or stimulation of the diaphragm. Such therapy may be implemented with either stimulation of the diaphragm directly, as with intramuscular electrode(s) embedded within the muscle, or through stimulation of one or both of the phrenic nerves, which contain the efferent motor axons innervating the diaphragm. Various therapies may call for delivery of stimulation to intercostals.

Various exemplary methods, devices and/or systems maintain knowledge of the timing of prior breaths, whether these breaths are wholly artificial, artificially augmented, or wholly natural (e.g., intrinsic). In this manner, when therapy is delivered, it may be delivered in phase with prior breaths, which may minimize need for artificial diaphragm activation. In turn, providing a minimal level of stimulation minimizes risk of either out of phase or of too high intensity stimulation, especially when such stimulation is delivered in a manner whereby a higher risk of airway occlusion exists.

While various exemplary methods mention use of respiration models, such as exponential decay or rise models, template matching may be used as well. For example, a signal such as the thoracic impedance may be monitored, and some running average amplitude and morphology (shape) of each respiratory cycle maintained. Then, once a breath exhibits a smaller impedance change during inspiration, an implanted device may implement an exemplary method that calls for artificial diaphragm activation in phase with intrinsic but inadequate inspiration.

Accordingly, various exemplary techniques described herein aim to adjust actual tidal volume during an evolving hypopnea associated CSR; whereas, if the evolving hypopneic phase of CSR was left untreated, it may diminish breath by breath and progress to a point until either frank apnea occurs (e.g., potentially inducing an arousal) or a natural rebound hyperpneic period of CSR (with or without a concomitant arousal) occurs. As described herein, various exemplary methods, devices and/or systems aim to terminate CSR or dampen oscillations through use of therapy that adjusts inspiration (e.g., via artificial diaphragm activation). Such therapy may call for delivery of stimulation for diaphragm activation during a decrescendo and/or a crescendo noting that delivery during either or both may help dampen oscillations in tidal volume.

Various exemplary methods, devices and/or systems optionally include one or more features described in the aforementioned co-pending application. For example, referring to the exemplary scenario 1100 of FIG. 11, another limit may exist above the limit 1112 wherein a different therapy is applied. Such a therapy may include calling for stimulation for diaphragm activation at an energy or power based on a difference between the actual tidal volume and the other limit or on the tidal volume or other respiration variable wherein energy or power may be based on a nonincreasing monotonic relationship with respect to increasing tidal volume; whereas, if tidal volume falls below the limit 1112, a change in therapy occurs whereby a call for stimulation may rely on a stimulation energy or power based on a nondecreasing monotonic relationship with respect to increasing tidal volume. Of course, a number of limits may be used that have one or more associated therapies such as those described herein, in the co-pending application and/or elsewhere. An exemplary method may include sensing respiratory information related to tidal volume, based at least in part on the respiratory information, determining if tidal volume is between an upper limit and a lower limit and, if the tidal volume is between the upper limit and the lower limit, calling for diaphragm activation at a stimulation power based on a nonincreasing monotonic relationship with respect to increasing tidal volume or, if the tidal volume is less than the lower limit, calling for diaphragm activation at a stimulation power based on a nondecreasing monotonic relationship with respect to increasing tidal volume.

Figure 15:
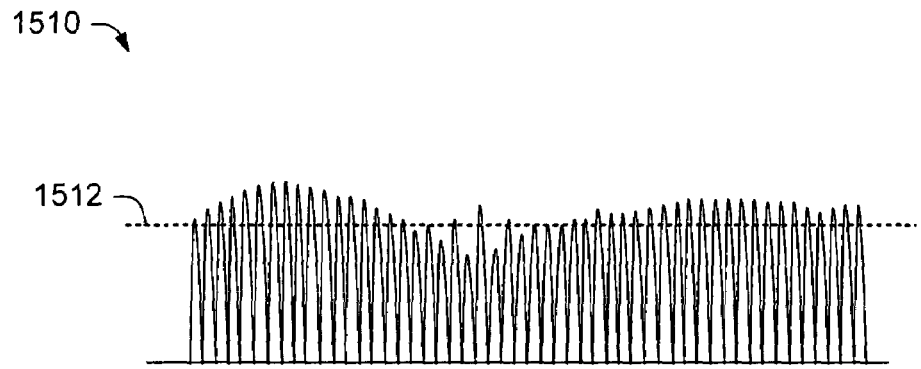
FIG. 15 is a diagram of an exemplary scenario showing various respiratory cycles and therapy in response thereto.
Figure 15:
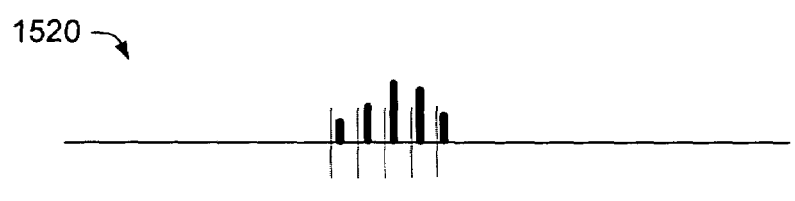
Figure 15:
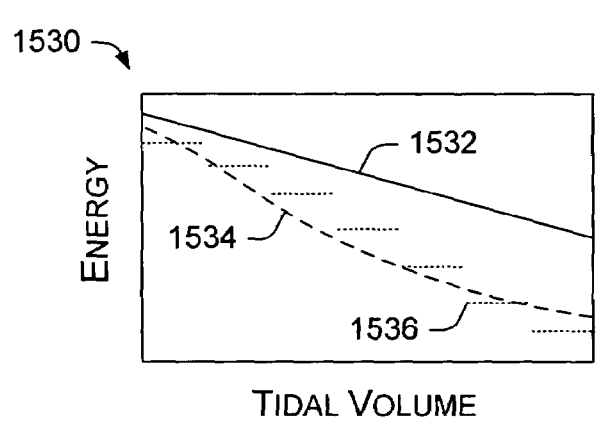

FIG. 15 shows an exemplary scenario 1500 that includes a plot of tidal volume versus time 1510, a plot of stimulation energy versus time 1520 and a plot of stimulation energy versus tidal volume 1530. The plot 1510 includes a limit 1512, for example, such as a respiration limit.

The limit 1512 may be used in a decision block of an exemplary maintenance method that decides, for example, on the basis of monitored characteristics (e.g., received and/or sensed information) and one or more limits, whether respiratory activity is sufficient. The one or more limits may rely on historical information such as an average of certain characteristics, etc. If such a decision block decides that intrinsic respiration is insufficient (e.g., insufficient tidal volume, etc.), then call for diaphragm activation based on the decrease in respiration may be made. For example, the decrease in respiration may be based on an error determination that determines an error between an indicator of actual respiration (e.g., a most recently received or sensed indicator) and a parameter or limit, which may be selected from one or more limits (e.g., a historical average of an indicator related to tidal volume, etc.).

In the scenario 1500, no action occurs for tidal volume that exceeds the limit 1512; however, such respiratory information may indicate that a patient is experiencing hyperpnea and that hypopnea could follow wherein tidal volume falls below the limit 1512. Indeed, at a time $T_1$, tidal volume falls below the limit 1512. Accordingly, an exemplary method delivers stimulation at an energy or a power (e.g., total energy over time) based on a nonincreasing monotonic relationship with respect to increasing tidal volume and/or decreasing error (e.g., error between a limit and actual tidal volume). Thus, in general, stimulation energy or power increases with decreasing tidal volume or increasing error (e.g., see the plot 1530).

The plot 1530 includes various relationships between energy or power and tidal volume. A linear relationship 1532 indicates that energy is linearly and inversely proportional to tidal volume or linearly proportional to error and may include an offset typical of a linear equation. A nonlinear relationship 1534 indicates that energy is nonlinear with respect to tidal volume. Such a relationship may be nonlinearly and inversely proportional with respect to tidal volume or nonlinearly proportional with respect to error. A step-wise relationship 1536 indicates that energy changes in one or more discrete steps with respect to tidal volume (e.g., energy or power may remain constant over a certain range of tidal volume) or error. As already mentioned, proportional includes linearly, nonlinearly and/or step-wise proportional. The various relationships 1532, 1534, 1536 of the plot 1530 are nonincreasing monotonic with respect to increasing tidal volume or decreasing error. Of course, other relationships may be possible, including those that are not nonincreasing monotonic with respect to increasing tidal volume or decreasing error. In general, a plot such as the plot 1530 may be independent of time. Other plots or relationships between energy or power and a respiration parameter may depend on time. In particular, a predictive model may rely on a time variable to predict future tidal volume or appropriate energy or power.

Referring again to the timings, at time $T_1$, a difference or error between the limit 1512 and the actual tidal volume exists. In this example, delivery of the stimulation occurs during inspiration of the next inspiratory phase. In general, especially for small errors, intrinsic activity is sufficient to generate airway patency capable of handling artificial diaphragm activation at an energy or power proportional to the error. As already mentioned, proportional may include linearly proportional, nonlinearly proportional and/or step-wise proportional. A linearly proportional relationship may typically be defined by use of a constant proportionality parameter. A nonlinear proportional relationship may rely on a constant and/or a variable proportionality parameter (e.g., a constant portion and a variable portion, etc.). Step-wise proportionality may include a linear and/or a nonlinear proportionality relationship and corresponding parameters, etc. In general, relationships are selected from those wherein stimulation energy or power abides by a nonincreasing monotonic relationship with respect to increasing tidal volume.

In the scenario 1500, the stimulation delivered after time $T_1$ causes an increase in tidal volume wherein the total tidal volume is approximately equal to the limit 1512; whereas, a subsequent respiratory cycle at time $T_2$ has a tidal volume that again falls below the limit 1512. Consequently, another call for stimulation occurs for diaphragm activation as indicated in the plot 1520 with energy or power based on, for example, one of the relationships 1532, 1534 or 1536. Similar behavior and response occurs at times $T_3$, $T_4$ and $T_5$. Overall, in this example, the stimulation for diaphragm activation during the hypopnea results in less hyperpnea. Further, calls for stimulation typically occur during a decrescendo and during a crescendo. In various alternative examples, stimulation may occur during a crescendo and/or a decrescendo. Yet further, a call for stimulation may occur based on a rise or slope-base limit wherein delivery of stimulation energy or power occurs during the inspiratory phase of the respiratory cycle that exhibits an insufficient rise in tidal volume over time. Various exemplary methods may rely on flow, tidal volume or other respiratory information that can indicate hypopnea and/or hypernea and optionally derivatives, integrals, etc., thereof.

While the scenario 1500 exhibits calling for artificial diaphragm activation in response to tidal volume due to inspiration not meeting a particular limit, a call for artificial diaphragm activation may also be in response to an expiration not meeting a particular limit or a combination of expirations and/or inspirations, etc., not meeting one or more limits. While the plot 1510 shows a baseline, such a baseline typically varies over time. In particular, not all breaths end or commence at the same tidal volume value.

While the plot 1510 indicates that augmentation achieves respiration similar to normal respiration, augmentation may achieve a greater respiration volume or a lesser respiration volume. For example, if a particular set of augmentation parameters do not avoid CSR, then such parameters may be adjusted in a manner whereby diaphragm activation achieves a respiration volume of about 110% or more of normal respiration volume.

In various examples, adjustment of a proportionality constant or other parameter used to determine one or more stimulation parameters may occur to increase energy or power level of phrenic nerve stimulation, direct diaphragm stimulation, etc. Of course, in such examples, monitoring of upper airway collapse may feedback to ensure that the energy or power level does not cause collapse and hence waste energy. If such exemplary mechanisms do not avoid CSR, for example, after a given period of time or number of respiratory cycles, then an alternative intervention, adjustment or therapy may occur. As discussed herein, the exemplary scenarios 1100 of FIG. 11 ("termination" therapy) and 1500 of FIG. 15 ("maintenance" therapy) may optionally be used in various exemplary tiered therapies. For example, various exemplary methods may select a termination therapy or a maintenance therapy as part of a tiered therapy. Further, other types of therapy may be included in such a tiered therapy (e.g., pacing, etc.). Yet further, within a type of therapy, various sub-tiers may exist. In some examples, movement between tiers or selection of a tier may rely on type of respiratory issue (e.g., central, obstructive, etc.). Of course, a tiered therapy may operate without regard to diagnosis of or classification of a respiratory issue. For example, a parameter may indicate whether a respiratory issue exists and whether the respiratory issue is improving or worsening, without a need to classify specifics of the respiratory issue.

Various exemplary mechanisms include overdrive pacing to maintain respiratory function, avoid apnea and/or hypopnea and/or terminate apnea and/or hypopnea. FIGS. 16-19 show various exemplary methods that optionally include tiered therapy wherein an early tier relies on overdrive pacing and wherein a latter tier may rely on diaphragm activation.

Figure 16:
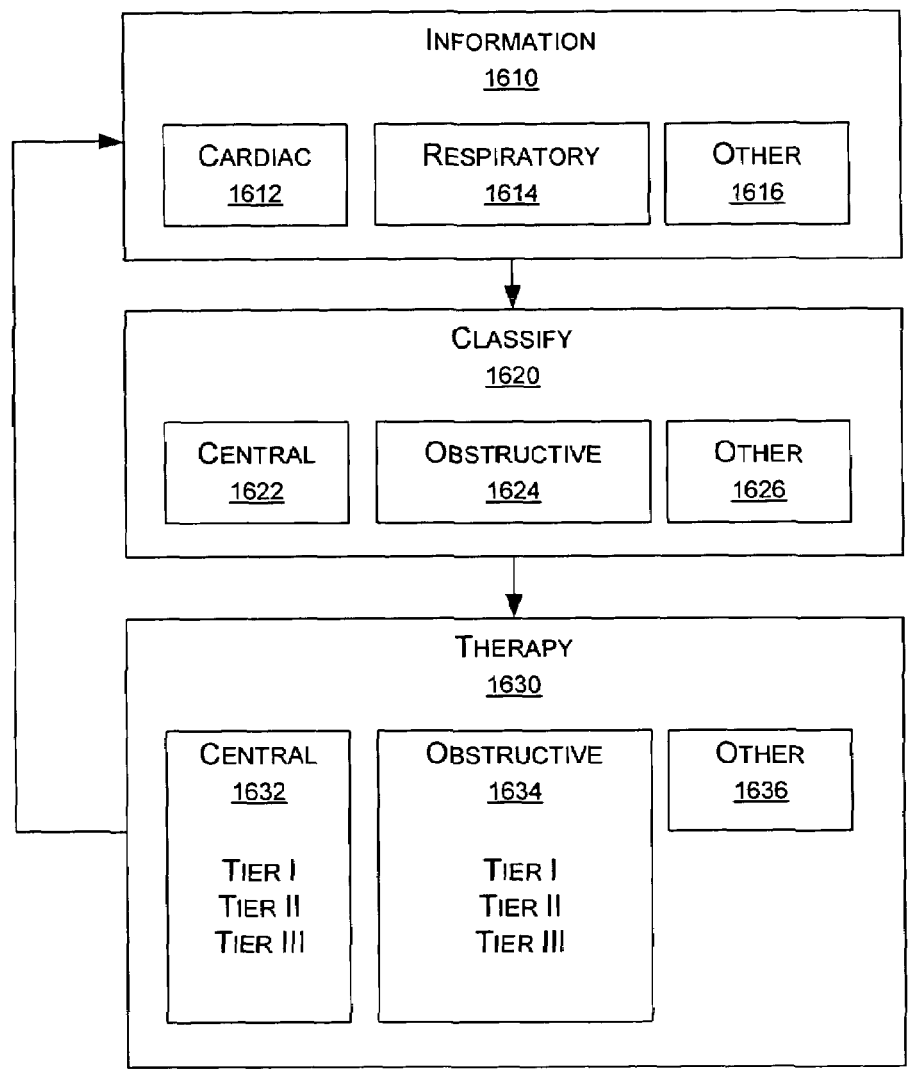
FIG. 16 is a block diagram of an exemplary method for acquiring information, classifying conditions and delivering therapy.

FIG. 16 shows a block diagram of an exemplary method 1600. The method 1600 includes an information block 1610, a classification block 1620 and a therapy block 1630. Application of therapy per the therapy block 1630 may generate additional information, which may be used to optimize therapy.

The information block 1610 may acquire information such as cardiac information 1612, respiratory information 1614 and other information 1616. The cardiac information 1612 may include intrinsic rate, pacing rate, cardiac output, blood pressure and other information related to cardiac function. The respiratory information 1614 may include tidal volume, phrenic nerve activity, upper airway patency and other information related to respiration. Other information, not directly related to cardiac function or respiration, may include patient activity, patient position, time of day, sleep time, etc.

According to the exemplary method 1600, information of the information block 1610 may be used to classify respiration and, in particular, apneic states. In general, apnea may be classified as central 1622 or obstructive 1624. Other classifications may also be possible 1626, which may or may not require intervention.

The therapy block 1630 includes therapies for central respiratory issues 1632, therapies for obstructive respiratory issues 1634 and other therapies 1636, as appropriate. For example, if a patient does not have a history of central respiratory issues, then a therapy block may not include therapies related to such issues. The central therapy block 1632 includes three tiers of therapy: Tier I, Tier II and Tier III. The obstructive therapy block 1634 includes three tiers of therapy: Tier I, Tier II and Tier III. Details of exemplary therapies are described further below which include overdrive pacing, diaphragm activation and/or other therapies.

Figure 17:
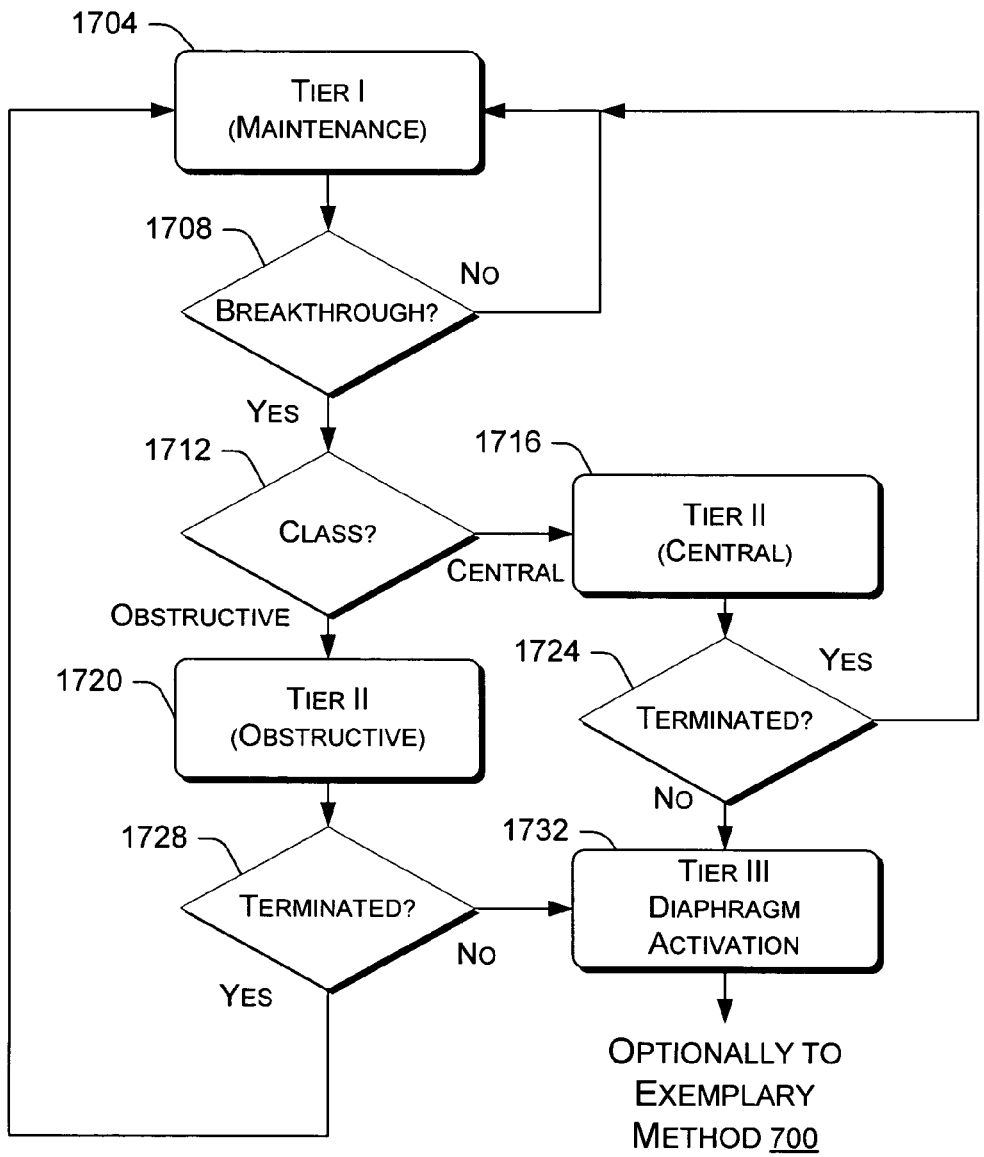
FIG. 17 is a block diagram of an exemplary method for delivering tiered therapy for maintenance and/or termination of various respiratory conditions.

FIG. 17 shows an exemplary method 1700 for delivering tiered therapy for respiratory issues. The exemplary method 1700 commences in a Tier I therapy block 1704, which pertains to maintenance. Maintenance refers to a therapy that aims to avoid respiratory issues such as occurrence of apnea, hypopnea, etc. In this example, a decision block 1708 is implemented during delivery of the Tier I maintenance therapy. The decision block 1708 decides whether breakthrough has occurred. Breakthrough refers to occurrence of a respiratory issue or condition during application of a maintenance therapy. If breakthrough occurs then a change in therapy may be appropriate, for example, a change to a higher tiered therapy.

Figure 18:
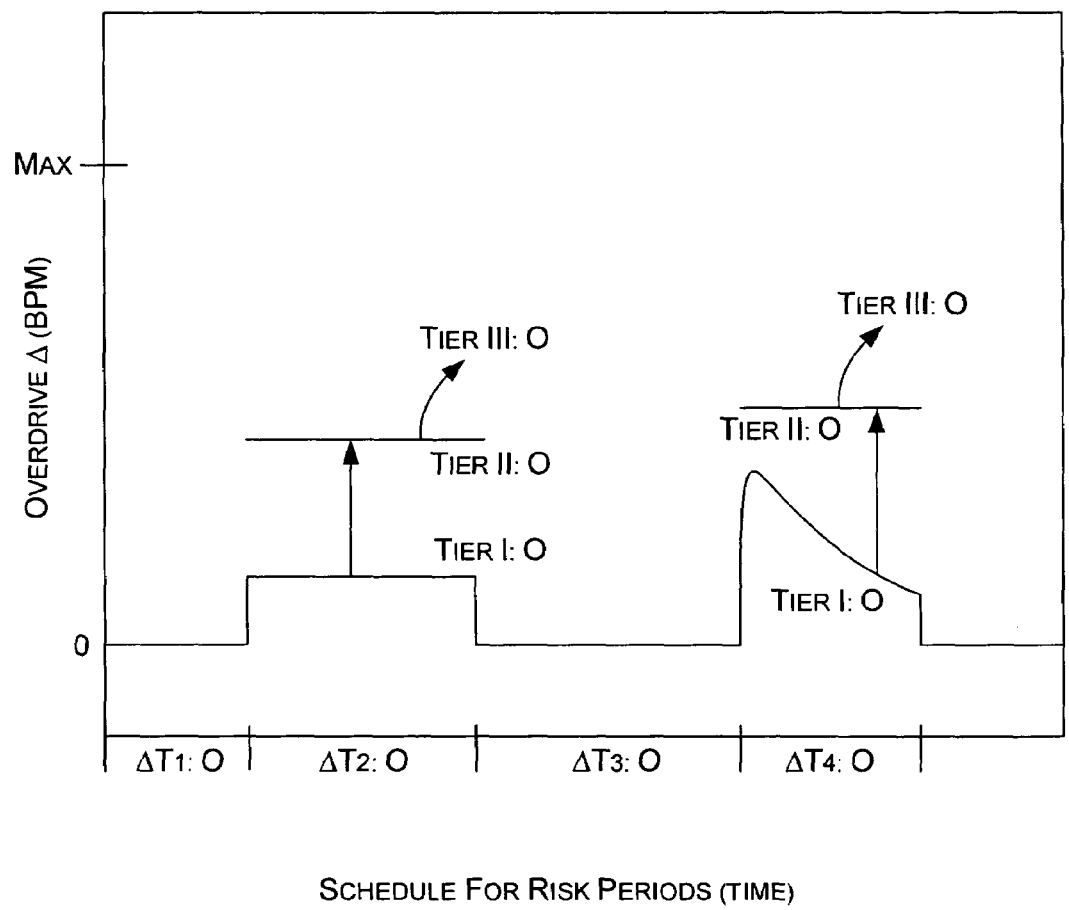
FIG. 18 is an exemplary method or schedule for delivery of tiered therapy for obstructive respiratory conditions.
Figure 19:
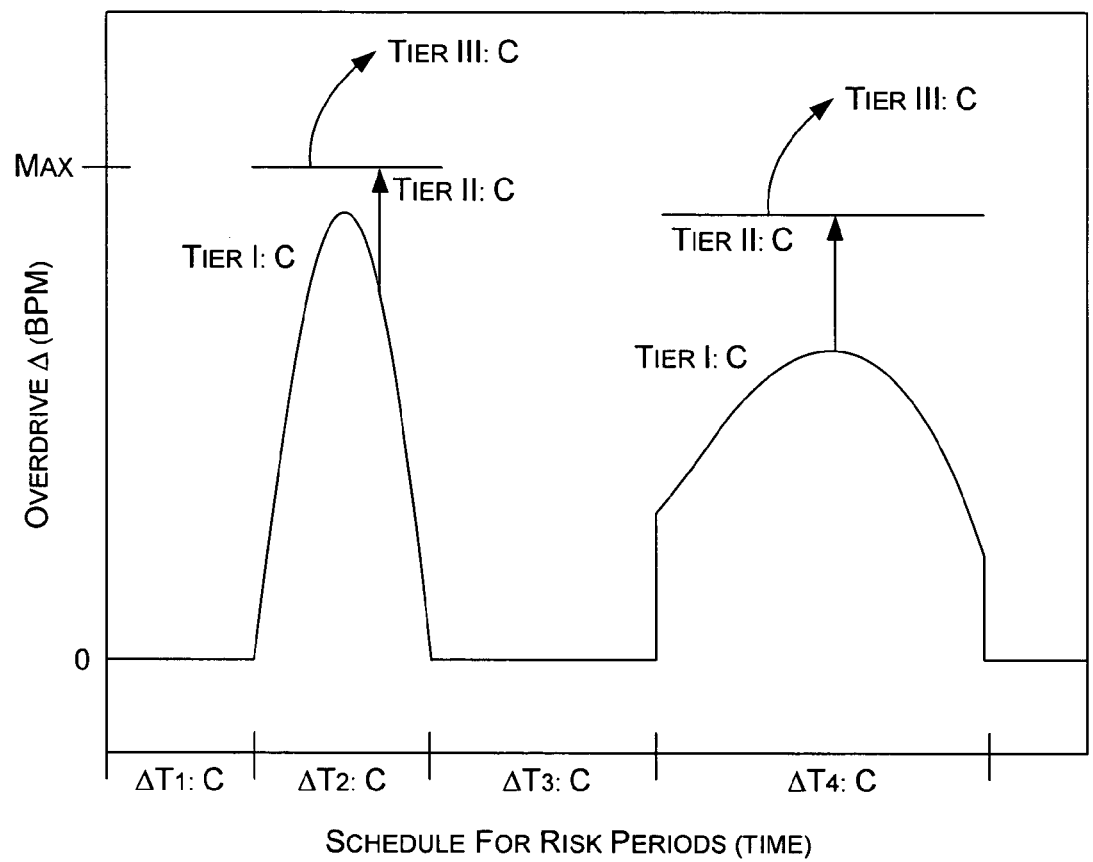
FIG. 19 is an exemplary method or schedule for delivery of tiered therapy for constructive respiratory conditions.

According to the method 1700, a classification block 1712 follows as a response to breakthrough. The classification block 1712 may rely on information (e.g., see the information block 1610 of FIG. 16) to classify the breakthrough issue as being related to central respiratory issues or as being related to obstructive respiratory issues. For example, if the classification block 1712 classifies the breakthrough as central apnea, then a Tier II block 1716 commences an appropriate therapy that aims to terminate central apnea. If the classification block 1712 classifies the breakthrough as obstructive apnea, then a Tier II block 1720 commences an appropriate therapy that aims to terminate obstructive apnea. In general, a therapy for termination of central apnea may be more aggressive that a therapy for termination of obstructive apnea. For example, a therapy for termination of central apnea may expend more power than a therapy for termination of obstructive apnea. FIGS. 18 and 19 describe various exemplary therapies that aim to maintain proper respiration and that aim to terminate detrimental respiratory conditions that may be optionally classified as obstructive or central, respectively.

Referring again to the exemplary method 1700 of FIG. 17, decision blocks 1720, 1724 occur in conjunction with respective Tier II therapy blocks 1716, 1720. Each of the decision blocks 1720, 1724 decides whether the applied Tier II therapy has terminated the associated breakthrough condition. If the Tier II therapy succeeded, then the method 1700 continues at the Tier I maintenance block 1704. However, if the Tier II therapy fails to terminate the condition, then the method 1700 commences a higher tier of therapy, a Tier III therapy block 1732, which may be common for both obstructive and central respiratory issues. In this example, the Tier III therapy block 1732 includes diaphragm activation, which optionally includes the exemplary method 700 of FIG. 7.

As the exemplary method 1700 proceeds, information pertaining to success, failure, timing (e.g., time of day), therapy parameters, etc., may be acquired and used to optimize any particular therapy (e.g., Tier I, Tier II, Tier III, etc.). For example, if breakthrough occurs at a particular time of night while a patient sleeps, then one or more parameters related to maintenance therapy may be adjusted accordingly.

FIG. 18 shows an exemplary method or schedule 1800 for applying therapies related to minimizing risk of obstructive respiratory conditions and termination of obstructive respiratory conditions. The schedule 1800 calls for overdrive pacing in excess of a base rate, a paced rate and/or an intrinsic rate. For example, an overdrive delta ($\Delta$) may vary from no therapy, a 0 bpm, to a maximum rate. The therapy may occur based on an event, time of day, etc. For example, "$\Delta$T1:O" may be a delay that occurs after a patient has reclined, as detected by a position or other sensor while "$\Delta$T2:O" corresponds to a duration for a maintenance therapy (e.g., "Tier I:O"). In this example, maintenance therapy calls for a substantially constant overdrive $\Delta$ over the duration $\Delta$T2:O.

During delivery of the maintenance therapy, various conditions may be monitored to determine if breakthrough has occurred. In the exemplary schedule 1800, the breakthrough therapy ("Tier II:O ") for the duration $\Delta$T2:O corresponds to a higher overdrive $\Delta$. Should this therapy fail to terminate the obstructive condition after, for example, a set duration, energy level, etc., then an even higher tier of therapy commences (e.g., "Tier III:O"). In this example, this higher tier of therapy, Tier III:O, corresponds to a therapy that optionally includes diaphragm activation and that may not include overdrive pacing.

After the duration $\Delta$T2:O, another duration commences $\Delta$T3:O, which does not include delivery of a maintenance therapy. However, should a respiratory issue arise during $\Delta$T3:O, then the prior therapy may be extended and/or a new maintenance therapy added to the schedule 1800.

Another maintenance therapy, Tier I:O, commences during the duration $\Delta$T4:O. This particular maintenance therapy may adjust dynamically to sensed information (see, e.g., the information block 1610 of FIG. 16) and/or be predetermined. For example, over the duration $\Delta$T4:O, the overdrive $\Delta$ increases in a substantially stepwise manner, decays substantially exponentially and then decreases to 0 bpm substantially stepwise. The corresponding higher tier therapy (e.g., "Tier II:O") for this particular duration corresponds to a higher overdrive $\Delta$. An even higher tier of therapy (e.g., "Tier III:O") may be the same as the Tier III:O therapy for the $\Delta$T2:O duration or it may differ.

The exemplary schedule 1800 illustrates various parameters that may be adjusted to optimize therapy and/or tiers of therapy for respiratory issues. In this particular example, the therapies include maintenance and termination therapies wherein the termination therapies optionally include diaphragm activation. The parameters may include energy, power, duration, parameters for dynamic response to underlying sensed information, parameters to determined preset profiles, parameters related to patient activity (e.g., sleep), etc. While the schedule 1800 shows various "upward" changes in tiered therapy, such an exemplary schedule may include "downward" changes and offer some degree of cycling, optionally with cycle limits.

FIG. 19 shows an exemplary method or schedule 1900 for applying therapies related to minimizing risk of central respiratory conditions and termination of central respiratory conditions. The schedule 1900 calls for overdrive pacing in excess of a base rate, a paced rate and/or an intrinsic rate. For example, an overdrive delta ($\Delta$) may vary from no therapy, a 0 bpm, to a maximum rate. The therapy may occur based on an event, time of day, etc. For example, "$\Delta$T1:C" may be a delay that occurs after a patient has reclined, as detected by a position or other sensor while "$\Delta$T2:C" corresponds to a duration for a maintenance therapy (e.g., "Tier I:C"). In this example, maintenance therapy calls for a substantially sine shaped overdrive $\Delta$ over the duration $\Delta$T2:C.

During delivery of the maintenance therapy, various conditions may be monitored to determine if breakthrough has occurred. In the exemplary schedule 1900, the breakthrough therapy ("Tier II:C") for the duration $\Delta$T2:C corresponds to a higher overdrive $\Delta$. Should this therapy fail to terminate the obstructive condition after, for example, a set duration, energy level, etc., then an even higher tier of therapy commences (e.g., "Tier III:C"). In this example, this higher tier of therapy, Tier III:C, corresponds to a therapy that optionally includes diaphragm activation and that may not include overdrive pacing.

After the duration $\Delta$T2:C, another duration commences $\Delta$T3:C, which does not include delivery of a maintenance therapy. However, should a respiratory issue arise during $\Delta$T3:C, then the prior therapy may be extended and/or a new maintenance therapy added to the schedule 1900.

Another maintenance therapy, Tier I:C, commences during the duration $\Delta$T4:C. This particular maintenance therapy may adjust dynamically to sensed information (see, e.g., the information block 1610 of FIG. 16) and/or be predetermined. For example, over the duration $\Delta$T4:O, the overdrive $\Delta$ increases in a substantially stepwise manner, rises and decays substantially monotonically and then decreases to 0 bpm substantially stepwise. The corresponding higher tier therapy (e.g., "Tier II:C") for this particular duration corresponds to a higher overdrive $\Delta$. An even higher tier of therapy (e.g., "Tier III:C") may be the same as the Tier III:C therapy for the $\Delta$T2:C duration or it may differ.

The exemplary schedule 1900 illustrates various parameters that may be adjusted to optimize therapy and/or tiers of therapy for respiratory issues. In this particular example, the therapies include maintenance and termination therapies wherein the termination therapies optionally include diaphragm activation.

In some instances, a termination therapy that aims to break an abnormal respiratory pattern may transition to a maintenance therapy after a certain number of respiratory cycles or after a time interval. Other indicators may also call for such a transition. While the schedule 1900 shows various "upward" changes in tiered therapy, such an exemplary schedule may include "downward" changes and offer some degree of cycling, optionally with cycle limits.

The exemplary device 100 of FIGS. 1 and 2 is optionally used to implement an exemplary method that includes tiered therapy for prevention and/or treatment of respiratory conditions. Such an exemplary device optionally includes features for diaphragm activation.

CONCLUSION

Although exemplary mechanisms (e.g., implemented as or in methods, devices, systems, software, etc.) have been described in language specific to structural features and/or methodological acts, it is to be understood that the subject matter defined in the appended claims is not necessarily limited to the specific features or acts described.

What is claimed is:
1. A method comprising:
   at a time corresponding to patient rest and in the absence of sleep apnea, delivering a maintenance therapy that aims to prevent sleep apnea, the maintenance therapy comprising cardiac overdrive pacing at a first overdrive rate in excess of a cardiac base rate, a cardiac paced rate or a cardiac intrinsic rate, where the overdrive pacing rate corresponds to an interval between atrial or ventricular pacing pulses;

sensing information during delivery of the maintenance therapy;

based at least in part on the information, determining if apnea comes into existence during delivery of the maintenance therapy; and if apnea comes into existence, stopping delivery of the maintenance therapy and delivering a termination therapy comprising overdrive pacing at a second overdrive rate in excess of the first overdrive rate.

2. The method of claim 1 further comprising classifying the apnea as being related to central apnea or obstructive apnea.

3. The method of claim 1 wherein delivering termination therapy further comprises delivering diaphragm activation.

4. The method of claim 1 wherein a time corresponding to patient rest is determined according to a schedule.

5. The method of claim 1 wherein a time corresponding to patient rest is determined by position information of a patient.

6. The method of claim 1 wherein a time corresponding to patient rest is determined by activity information of a patient.

7. The method of claim 1 further comprising adjusting one or more parameters associated with the maintenance therapy in response to the determining.

8. The method of claim 1 wherein overdrive pacing is delivered at a constant rate as a function of time.

9. The method of claim 1 wherein overdrive pacing is delivered at a nonconstant rate as a function of time.

10. The method of claim 9 wherein the nonconstant rate comprises one or more of an exponentially decaying component and a sine shaped component.

11. A method comprising:
at a time corresponding to patient rest and in the absence of sleep apnea, delivering a maintenance therapy that aims to prevent sleep apnea, the maintenance therapy comprising cardiac overdrive pacing at a first overdrive rate in excess of a cardiac base rate, a cardiac paced rate or a cardiac intrinsic rate;

sensing information during delivery of the maintenance therapy;

based at least in part on the sensed information, determining if apnea comes into existence during delivery of the maintenance therapy; and if apnea comes into existence, stopping delivery of the maintenance therapy and delivering a termination therapy comprising diaphragm activation.

12. A method comprising:
at a time corresponding to patient rest and in the absence of hypopnea, delivering a maintenance therapy comprising cardiac overdrive pacing at a first overdrive rate in excess of a cardiac base rate, a cardiac paced rate or a cardiac intrinsic rate, that aims to prevent occurrence of hypopnea;

sensing information during delivery of the maintenance therapy;

based at least in part on the information, determining if hypopnea comes into existence during delivery of the maintenance therapy; and if hypopnea comes into existence, stopping delivery of the maintenance therapy and delivering a termination therapy that aims to terminate the hypopnea.

13. The method of claim 12 wherein the termination therapy comprises overdrive pacing at a second overdrive rate in excess of the first overdrive rate.

14. The method of claim 12 wherein the sensing information comprises sensing information related to airway patency.

15. The method of claim 12 further comprising delivering diaphragm activation if the termination therapy fails to terminate the hypopnea.

16. The method of claim 12 wherein a time corresponding to patient rest is determined according to a schedule.

17. The method of claim 12 a time corresponding to patient rest is determined by position information of a patient.

18. The method of claim 12 wherein a time corresponding to patient rest is determined by activity information of a patient.

19. The method of claim 12 further comprising adjusting one or more parameters associated with the maintenance therapy in response to the determining.

20. The method of claim 12 wherein the termination therapy comprises diaphragm activation.

21. The method of claim 12 wherein the maintenance therapy comprises diaphragm activation.

* * * * *